United States Patent
Nozaki

(10) Patent No.: US 8,940,532 B2
(45) Date of Patent: Jan. 27, 2015

(54) BIOLOGICAL GRAFT TRANSFERRING INSTRUMENT AND METHOD FOR TRANSFERRING BIOLOGICAL GRAFT

(75) Inventor: Yusuke Nozaki, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 431 days.

(21) Appl. No.: 13/171,931

(22) Filed: Jun. 29, 2011

(65) Prior Publication Data

US 2012/0000745 A1 Jan. 5, 2012

(30) Foreign Application Priority Data

Jun. 30, 2010 (JP) ................................. 2010-148873
Apr. 27, 2011 (JP) ................................. 2011-098992

(51) Int. Cl.
| | | |
|---|---|---|
| C12M 1/00 | (2006.01) | |
| C12M 1/26 | (2006.01) | |
| C12M 3/00 | (2006.01) | |
| A61B 17/00 | (2006.01) | |
| A61M 37/00 | (2006.01) | |
| A61F 2/24 | (2006.01) | |
| A61F 13/00 | (2006.01) | |
| A61K 9/00 | (2006.01) | |

(52) U.S. Cl.
CPC ............. *A61M 37/00* (2013.01); *A61B 17/00* (2013.01); *A61F 2/24* (2013.01); *A61F 13/00* (2013.01); *A61K 9/00* (2013.01); *A61B 2017/00969* (2013.01); *A61M 2202/09* (2013.01)
USPC ......... 435/309.1; 435/283.1; 606/79; 606/84; 606/86

(58) Field of Classification Search
USPC .................. 435/283.1–309.4; 606/79, 84, 86
See application file for complete search history.

(56) References Cited

U.S. PATENT DOCUMENTS

2006/0271070 A1 11/2006 Eriksson et al.
2008/0294093 A1 11/2008 Maeda et al.

FOREIGN PATENT DOCUMENTS

| CN | 1753648 A | 3/2006 |
|---|---|---|
| JP | 2007-222153 A | 9/2007 |
| JP | 2009-000511 A | 1/2009 |
| JP | 2009-072209 A | 4/2009 |
| WO | 2004006831 A2 | 1/2004 |
| WO | WO 2004/006831 A2 | 1/2004 |
| WO | 2004075764 A1 | 9/2004 |

OTHER PUBLICATIONS

Chinese Office Action dated Jan. 4, 2013, issued by the Chinese Patent Office in corresponding Chinese Patent Application No. 201110185032.X. (5 pages).
Extended European Search Report dated Dec. 22, 2011, issued by the European Patent Office in the corresponding European Application No. 11172068.6.

*Primary Examiner* — Nathan A Bowers
*Assistant Examiner* — Lydia Edwards
(74) *Attorney, Agent, or Firm* — Buchanan Ingersoll & Rooney PC

(57) ABSTRACT

A biological graft transferring instrument for transferring a biological graft includes a main body, a displacement member capable of being displaced relative to the main body, and a belt-shaped member which is wound around the forward end and base end of the displacement member and is joined to the main body. The biological graft is placed on the belt-shaped member at the forward end of the displacement member.

15 Claims, 20 Drawing Sheets

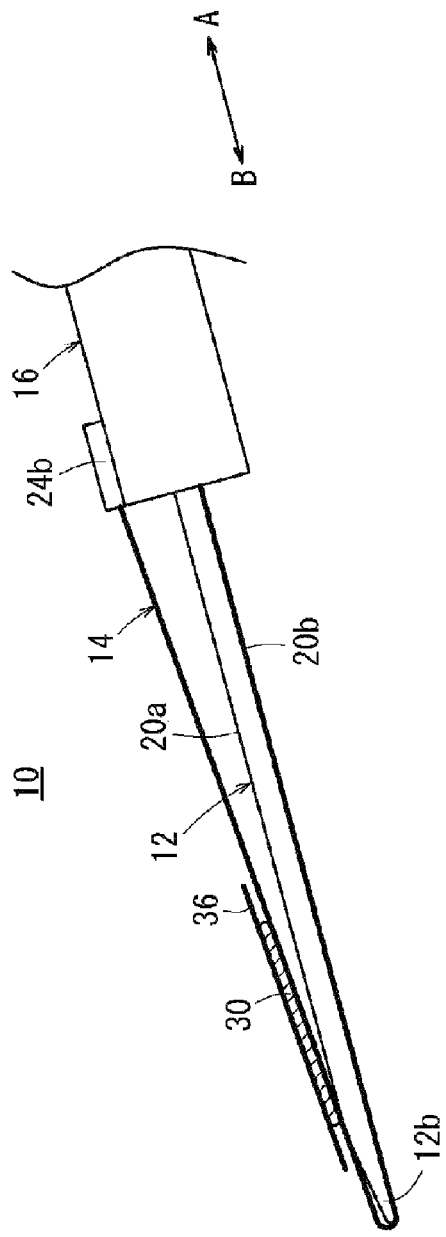
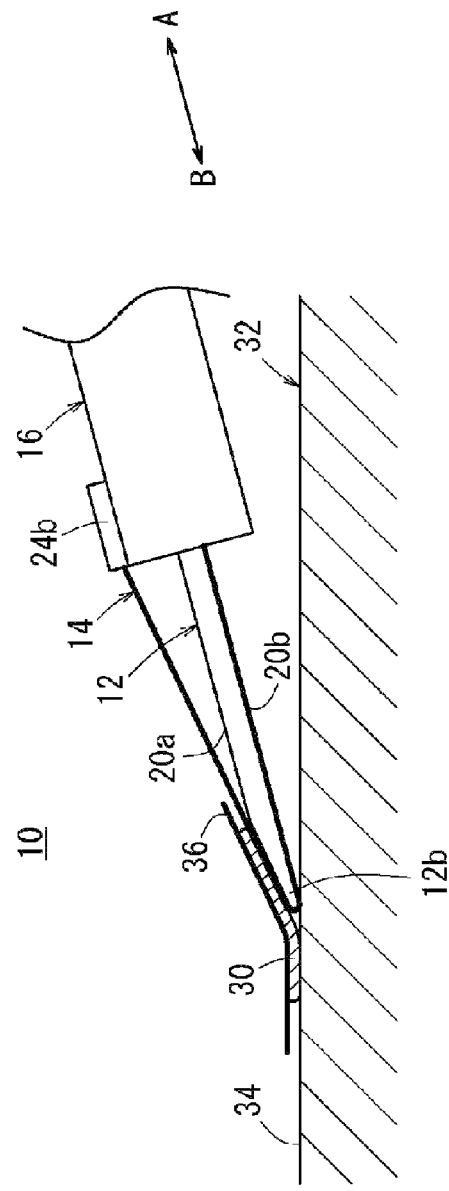
FIG. 7A
FIG. 7B

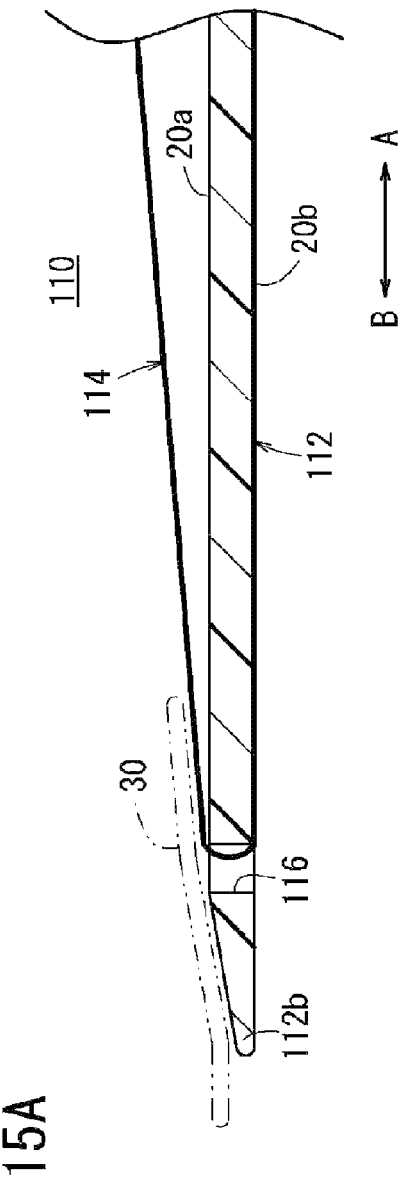
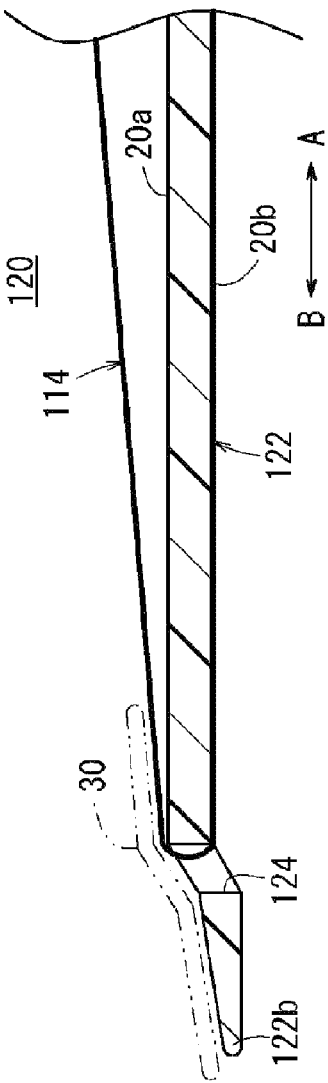
FIG. 15A
FIG. 15B

BIOLOGICAL GRAFT TRANSFERRING INSTRUMENT AND METHOD FOR TRANSFERRING BIOLOGICAL GRAFT

TECHNOLOGICAL FIELD

The present invention generally relates to a medical instrument and more particularly involves a biological graft transferring instrument and a method for transferring a biological graft, with the instrument and method being intended to transfer a biological graft to a desired position for medical treatment.

BACKGROUND DISCUSSION

One recent method for therapy of myocardial infarction involves transplantation of a sheet-like cell culture as a biological graft (which is a tissue obtained by cultivation of the patient's own cells) to the affected part. The sheet-like cell culture needs a skilful maneuver to take it out of the culture dish and transfer it to the affected part, because it is a fragile thin film and it quite easily sticks to itself on account of its water content. Thus, its transfer needs a special instrument.

One transferring instruments has a hollow outer cylinder and a sliding member slidably installed therein, the sliding member being provided with a flat flexible sheet-supporting member at the forward end of the sliding member. The sheet-supporting member is installed in such a way that it is held in the outer cylinder as the sliding member is moved relative to the outer cylinder. The transferring instrument works in such a way that the sheet-supporting member has a sheet-like cell culture placed thereon while it is outside the outer cylinder, and it is retracted so that the sheet-like cell culture is taken in the outer cylinder. Then, the forward end of the outer cylinder is moved to a position close to the affected part and the sliding member is pushed forward so that the sheet-like cell culture is transplanted to the affected part. An example of this instrument is described in Japanese Patent Laid-open No. 2009-511.

The transferring instrument mentioned above is capable of transferring a sheet-like cell culture. Nevertheless, it would be desirable to provide an improved instrument which is configured to facilitate mounting a sheet-like cell culture.

SUMMARY

The biological graft transferring instrument and method disclosed here possesses a relatively simple construction, yet is capable of holding a sheet-shaped cell culture relatively firmly and easily and transferring it to any desired position.

The biological graft transferring instrument includes a main body, a displacement member capable of being displaced relative to the main body, and a belt-shaped member which is wound around the forward end and base end of the displacement member and is connected to the main body, the biological graft is placed on the belt-shaped member at the forward end of the displacement member.

The instrument includes a main body, a displacement member, and a belt-shaped member. The main body holds the displacement member in such a way that the former permits the latter to move freely. The belt-shaped member is wound around the forward end and base end of the displacement member and is connected to the main body. The displacement member is displaced relative to the main body, so that the displacement causes the belt-shaped member to move back and forth. The displacement member is held by the belt-shaped member.

Accordingly, the displacement member and the belt-shaped member are displaced so that the belt-shaped member at the forward end of the displacement member holds a biological graft thereon. Then, the displacement member is displaced in the opposite direction so that the forward end thereof is retracted relative to the biological graft placed on the forward end thereof. In this way, the biological graft can be placed on the affected part. In other words, the instrument according to the present invention permits a sheet-shaped cell culture to be transferred securely and stably by simple operation of moving back and forth the displacement member relative to the main body while the forward end of the displacement member is in contact with the biological graft or while the biological graft is already placed on the belt-shaped member.

Having the main body, the displacement member, and the belt-shaped member, the biological graft transferring instrument can be produced at a relatively low production cost.

The displacement member may be provided with an operation section to be used to move the displacement member relative to the main body at the base end of the displacement member. The operation section permits the displacement member to be moved securely when the operator transfers a biological graft by means of the biological graft transferring instrument.

In addition, the belt-shaped member may have a holding surface made of a hydrophilic material that holds a biological graft thereon. This holding surface stably holds a water-containing biological graft thereon without repelling it.

Moreover, the belt-shaped member may have projections projecting from the holding surface that are capable of holding or sticking into the biological graft. Such projections stick into a biological graft when the belt-shaped member is moved backward and forward so that they are in a position to approach the biological graft. Thus the projections permit the biological graft to be mounted and held securely and stably on the holding surface.

The operation section is formed in a three-dimensional rectangular parallelepiped which is connected with the base end of the displacement member passing through the inside thereof. The operator can grip and stably operate the operation section when transferring a biological graft. By moving the main body back and forth while gripping the operation section, the operator can mount a biological graft on the belt-shaped member or transfer it from the belt-shaped member without changing the distance between the operation section on hand and the forward end of the displacement member.

The displacement member is further constructed in a hollow shape from the forward end, the base end, and the paired frames joining together the forward end and the base end. This hollow structure surely prevents the belt-shaped member wet with water from tightly sticking to the displacement member when the biological graft transferring instrument is in operation. In other words, it ensures smooth operation for the displacement member and the belt-shaped member without increase in their sliding resistance even though they are wet.

The gist of the present invention also resides in a method for transferring a biological graft to a desired position by using a biological graft transferring instrument. The method includes arranging the forward end of the instrument, with a belt-shaped member wound around it, near the biological graft, moving back and forth the belt-shaped member by means of a displacement member, which is displaceably arranged inside the belt-shaped member, thereby removing the biological graft from the surface supporting it and mounting it on the belt-shaped member, and transferring the biological graft to a desired position.

According to the method of the present invention, the transfer of a biological graft is accomplished as follows. First, the forward end of the biological graft transferring instrument is arranged near a biological graft to be transferred. Then, the displacement member is moved back and forth, so that the biological graft is mounted on the belt-shaped member. Finally, the displacement member is moved back and forth again, so that the biological graft is transferred to a desired position. Thus, the biological graft is transferred securely and stably through the belt-shaped member from the surface on which it is mounted to a desired position.

The foregoing method of the present invention may further include placing a thin film (a sheet body in a thin film form) on the biological graft and moving back and forth the belt-shaped member by means of a displacement member, which is displaceably arranged inside the belt-shaped member, thereby removing the biological graft together with the thin film from the belt-shaped member and transferring them to a desired position.

The foregoing modified method permits the biological graft to be transferred together with a thin film placed thereon. Transfer in this way would be more desirable than transfer of a biological graft alone because the thin film prevents the biological graft from being caught by the forward end of the belt-shaped member and also suitably protects the biological graft from damage during transfer.

The biological graft transferring instrument disclosed here is constructed of a main body, a displacement member, and a belt-shaped member which is wound around the forward end and base end of the displacement member. It works in such a way that as the displacement member is displaced relative to the main body, the belt-shaped member moves back and forth with the displacement member. It permits a sheet-shaped cell culture to be transferred securely and stably by a simple operation of moving the displacement member back and forth relative to the main body while the forward end of the displacement member is in contact with a biological graft or while the belt-shaped member has supported a biological graft thereon.

BRIEF DESCRIPTION OF THE DRAWINGS

FIG. 7A is an enlarged cross-sectional view of the forward end portion of the biological graft transferring instrument shown in FIG. 6, and FIG. 7B is an illustration of the biological graft transferring instrument in operation as shown in FIG. 7A, with the sheet-shaped cell culture being transplanted to the patient's affected part from the belt-shaped member.

FIG. 15A is an enlarged cross-sectional view of the forward end portion of the biological graft transferring instrument shown in FIG. 14, and FIG. 15B is an enlarged cross-sectional view of a modified embodiment of the biological graft transferring instrument shown in FIG. 15A.

DETAILED DESCRIPTION

Embodiments of the biological graft transferring instrument and method disclosed here by way of example are described below in more detail with reference to the accompanying drawings.

Figure 1:
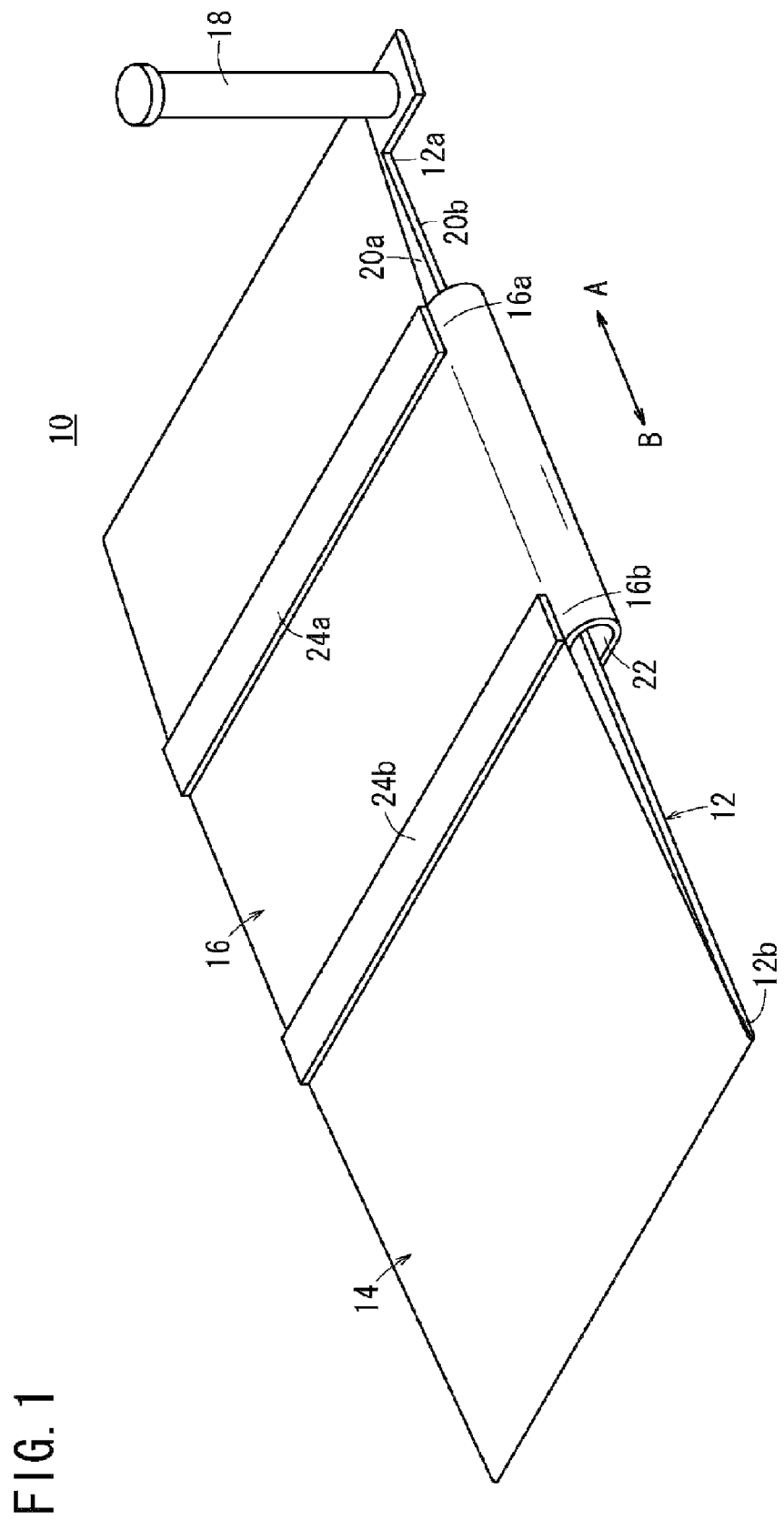
FIG. 1 is an external perspective view of one embodiment of the biological graft transferring instrument disclosed by way of example here.
Figure 2:
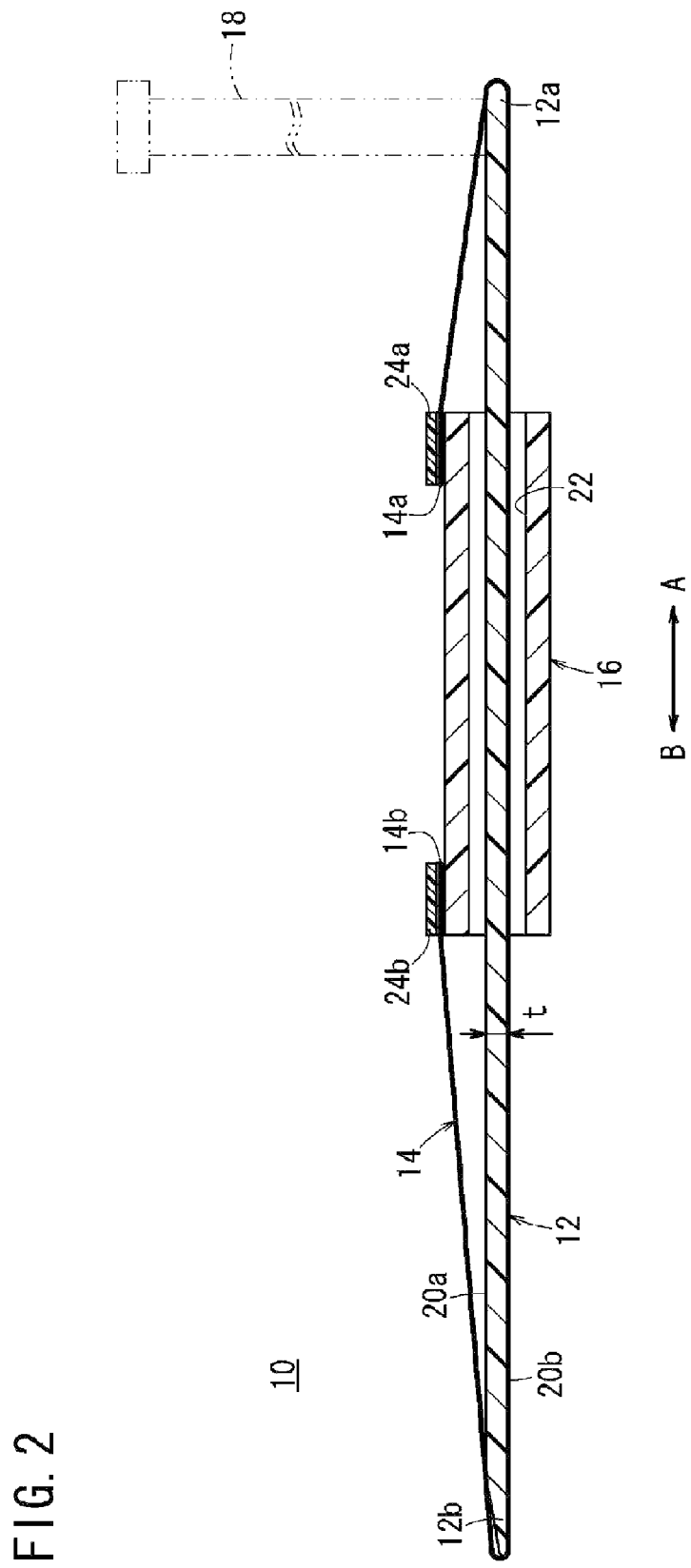
FIG. 2 is a longitudinal cross-sectional view of the biological graft transferring instrument shown in FIG. 1.

As shown in FIGS. 1 and 2, the biological graft transferring instrument 10 includes a plate-shaped supporting member (displacement member) 12, a belt-shaped member 14 extending around or wound around the supporting member 12 in its longitudinal direction, and a holding member (main body) 16 which freely moves along the supporting member 12, with both ends of the belt-shaped member 14 connected to the holding member. The directions A and B (or the right and left sides) indicated by the arrows FIGS. 1 and 2 denote respectively the "base end 12a" and the "forward end 12b" of the biological graft transferring instrument 10. This convention also applies to the other drawings.

The supporting member 12 is a flat rectangular object, with a generally uniform thickness of "t" as shown in FIG. 2, which is formed from a sheet of plastic material or metal material. To be more specific, the supporting member 12 is formed from a sheet (about 1 mm thick) of, for example, acrylic resin, vinyl chloride resin, aluminum alloy and stainless steel. In other words, the supporting member 12 is only required to have a certain strength and a certain thickness (t) to operate as intended as described below. The thickness (t) should be less than 5 mm, preferably less than 1 mm, and more preferably less than 0.5 mm.

The forward end 12b of the supporting member 12 should preferably be formed from a flexible plastics material. In other words, the forward end 12b of the supporting member 12 should be flexible enough to permit the belt-shaped member 14 to slide on the forward end 12b of the supporting member 12, and yet rigid enough to support a sheet-shaped cell culture (biological graft) 30. Because of this structure, the forward end 12b of the supporting member 12 properly bends even though it comes into contact with an affected part (desired position) 34 when the biological graft transferring instrument 10 transfers the sheet-shaped cell culture 30 to the affected part 34. This helps ensure safe operation without damage to the affected part 34.

Alternatively, the supporting member 12 can be constructed so that not only the forward end 12b of the supporting member 12 is formed from a flexible plastics material, but also the entirety of the supporting member 12 is formed from a flexible plastics material. Moreover, the forward end 12b of the supporting member 12 may be formed partly thinner than the remainder so that it relatively easily bends.

The supporting member 12 includes an operation section 18 attached to the laterally extended part of the base end 12a of the supporting member 12. The operation section 18 is a grippable upstanding member that is upstanding relative to the supporting member 12. The operation section includes a central axis that is transverse (perpendicular) to the plane in which the supporting member 12 lies so that the axis of the operation section 18 does not lie in a common plane with the supporting member 12. Stated differently, the operation section 18 extends in the direction perpendicular to the lengthwise direction (the directions A and B of the arrow) of the supporting member 12. The operator is able to operate the biological graft transferring instrument 10 by gripping the operation section 18.

The supporting member 12 may have its front surface 20a and back surface 20b coated with a hydrophobic material (such as fluoroplastics) or a hydrophilic material. The hydrophobic material causes the front surface 20a and the back surface 20b of the supporting member 12 to repel water from the front and back surfaces 20a, 20b or to form water drops on front and back surfaces 20a, 20b. In other words, the hydrophobic material is a material which increases the contact angle with water. On the other hand, the hydrophilic material makes the front surface 20a and the back surface 20b of the supporting member 12 compatible with water so that they do not repel water on the front and back surfaces 20a, 20b and do not form water drops on the front and back surfaces 20a, 20b. In other words, the hydrophilic material denotes a material which decreases the contact angle with water.

The coating with a hydrophobic material or a hydrophilic material on the front surface 20a and the back surface 20b of the supporting member 12 reduces sliding resistance between the supporting member 12 and the belt-shaped member 14, thereby allowing the belt-shaped member 14 to relatively smoothly slide on the supporting member 12. The noted coatings thus improve the slidability of the belt-shaped member 14 relative to the supporting member 12.

The belt-shaped member 14 is a thin sheet which extends in the lengthwise direction (in the directions of arrows A and B) of the supporting member 12 in such a way that the belt-shaped member 14 covers the forward end 12b and the base end 12a of the supporting member 12, and the belt-shaped member 14 is wound along the front surface 20a and the back surface 20b of the supporting member 12. That is, the belt-shaped member 14 covers or overlies the back surface 20b of the supporting member 12 as well as the portion of the front surface 20a of the supporting member 12 not covered by the holding member 16 as shown in FIG. 2. The belt-shaped member 14 has a width approximately equal to or slightly smaller than that of the supporting member 12. The belt-shaped member 14 is wound around (extends around) the supporting member 12 such that it contacts the forward end 12b and the base end 12a of the supporting member 12.

More specifically, the belt-shaped member 14 includes opposite ends (first and second ends) secured to the holding member 16 so that the two ends of the belt-shaped member 14 are fixed in place relative to the holding member and relative to each other. Beginning at the first end of the belt-shaped member 14 (e.g., the end closer to the forward end 12b of the supporting member 12), the belt-shaped member 14 includes extends towards the forward end 12b of the supporting member 12, extends or wraps around the forward end 12b of the supporting member 12, extends to the base end 12a of the supporting member 12, extends or wraps around the base end 12a of the supporting member 12 and terminates at the second end of the belt-shaped member 14. The portion of the belt-shaped member 14 between the first end of the belt-shaped member 14 and the forward end 12b of the supporting member 12 is taut and faces one surface of the supporting member 12, the portion of the belt-shaped member 14 between the forward end 12b of the supporting member 12 and the base end 12a of the supporting member 12 is taut and faces the opposite surface of the supporting member 12, and the portion of the belt-shaped member 14 between the base end 12a of the supporting member 12 and the second end of the belt-shaped member 14 is taut and faces the one surface of the supporting member 12.

The belt-shaped member 14 is a polymeric film formed from plastics material including polyethylene terephthalate (PET) and polyolefin resins such as polyethylene (PE) and polypropylene (PP). It has a thickness less than 0.2 mm, preferably less than 0.05 mm. The belt-shaped member may be formed from material other than those mentioned above which can be made sufficiently thin while possessing relatively high mechanical strength, low frictional coefficient, and adequate stiffness to resist twisting.

The belt-shaped member 14 should preferably have a hydrophilic outer surface so that it relatively easily carries the sheet-shaped cell culture 30 mentioned later. For example, the belt-shaped member 14 may be coated with a hydrophilic material, which makes the surface of the belt-shaped member 14 compatible with water so that the surface does not repel water or does not form water drops, decreasing the contact angle with water.

Hydrophilic material is generally classified into two broad categories: amphipathic substances (such as surface active agents) and hydrophilic natural and synthetic high polymers and mixtures thereof. Non-limiting examples of the surface active agents include ionic ones, such as sodium salt of fatty acid, monoalkyl sulfate, alkylpolyoxyethylene sulfate, alkyltrimethylammonium salt, dialkyldimethylammonium salt, alkyldimethylamineoxide, and alkylcarboxybetain and non-ionic ones, such as polyoxyethylene alkyl ether, fatty acid sorbitan ester, alkylpolyglucoside, fatty acid diethanolamide, and alkylmonoglyceryl ether.

Non-limiting examples of the hydrophilic natural polymers include proteins, such as fibrin gel, fibronectin, laminin, collagen, and gelatin, polysaccharides, such as agar-agar, carrageenan, and starch, nucleic acids, and peptides.

Non-limiting examples of the hydrophilic synthetic polymers include derivatives of natural polymers (such as carboxymethyl cellulose), polyacrylamide, polydimethyl acrylamide, polyacrylic acid and salt thereof, polyhydroxethyl methacrylate, polyhydroxyethyl acrylate, polyvinyl alcohol, polyvinyl pyrrolidone, polylatic acid, polyethylene glycol, and polyisopropyl acrylamide.

These substances may be directly applied or bound in any or by any means including a chemical bond to the outer surface of the belt-shaped member 14.

The inner surface of the belt-shaped member 14 may also be coated with a hydrophobic material (such as fluoroplastics) or a hydrophilic material. The hydrophobic material causes the inner surface of the belt-shaped member 14 to repel water from the inner surface of the belt-shaped member 14 or to form water drops on the inner surface of the belt-shaped member 14, owing to its relatively large contact angle with water. In contrast, the hydrophilic material makes the inner surface of the belt-shaped member 14 highly compatible with water (without repelling water or making water drops), owing to its relatively small contact angle with water.

Coating the inner surface of the belt-shaped member 14 with a hydrophilic or hydrophobic material helps reduce sliding resistance between the belt-shaped member 14 and the supporting member 12. It also prevents the inner surface of the belt-shaped member 14 from sticking to the front surface 20a and the back surface 20b of the supporting member 12. As a result, the belt-shaped member 14 slides relatively smoothly on the supporting member 12.

The holding member 16 is a component having a flat elongated rectangular cross-section. It has an opening hole 22 at its center that permits the supporting member 12 to pass completely through. Owing to this configuration, the holding member 16 can freely move in the lengthwise direction (the directions A and B of the arrow) of the supporting member 12 that passes through the opening hole 22. During movement, the holding member 16 is stably positioned a certain distance away from the supporting member 12 by guide means (not shown) installed in the supporting member 12.

The forward end 16b of the holding member 16 is fixed to one end 14b of the belt-shaped member 14 wound around the supporting member 12. Fixing is preferably accomplished by fusion, adhesion, or pressing by the plate 24b. The base end 16a of the holding member 16 is fixed to one end 14a of the belt-shaped member 14 wound around the supporting member 12. Fixing is preferably accomplished by fusion, adhesion, or pressing by the plate 24a. While holding the holding member 16, the operator moves the supporting member 12 back and forth in its lengthwise direction by the operation section 18, so that the belt-shaped member 14 turns around the outside of the supporting member 12. The belt-shaped member 14 is a curved, generally circular component, with its ends connected to the holding member 16, which covers the front surface 20a and the back surface 20b of the supporting member 12.

The biological graft to be transferred by the instrument and method described above is the cell culture 30 mentioned above, which can be prepared by any known method. In the illustrated embodiment, the cell culture 30 is a sheet-shaped cell culture 30.

The biological graft is composed of cultivated cells and/or products of cultivated cells. It may optionally contain a variety of materials to supplement and/or support a desired part, for example, an affected part or any other specific part of the living body. Moreover, the biological graft is typically one which is used for medical treatment of diseases and wounds of mammals including human and livestock. It will also find other uses. The biological graft may take on any shape, such as sheet, film, bulk, and column. During storage, it may normally contain water in an amount more than 70%, preferably more than 80%, more desirably more than 90%. It may also be stored in such a way that it is entirely or partly in contact with water.

The biological graft may be a single one or a group of several biological grafts. A typical example of the latter is a group of samples belonging to the same lot, though it is not limited in this regard.

The biological graft transferring instrument 10 according to this embodiment is constructed as described. Its operation and manner of use are described below, assuming that it is used to transfer the sheet-shaped cell culture 30, which has been cultivated in the culture dish 28 shown in FIG. 3, to the affected part 34 of the patient 32.

Figure 3:
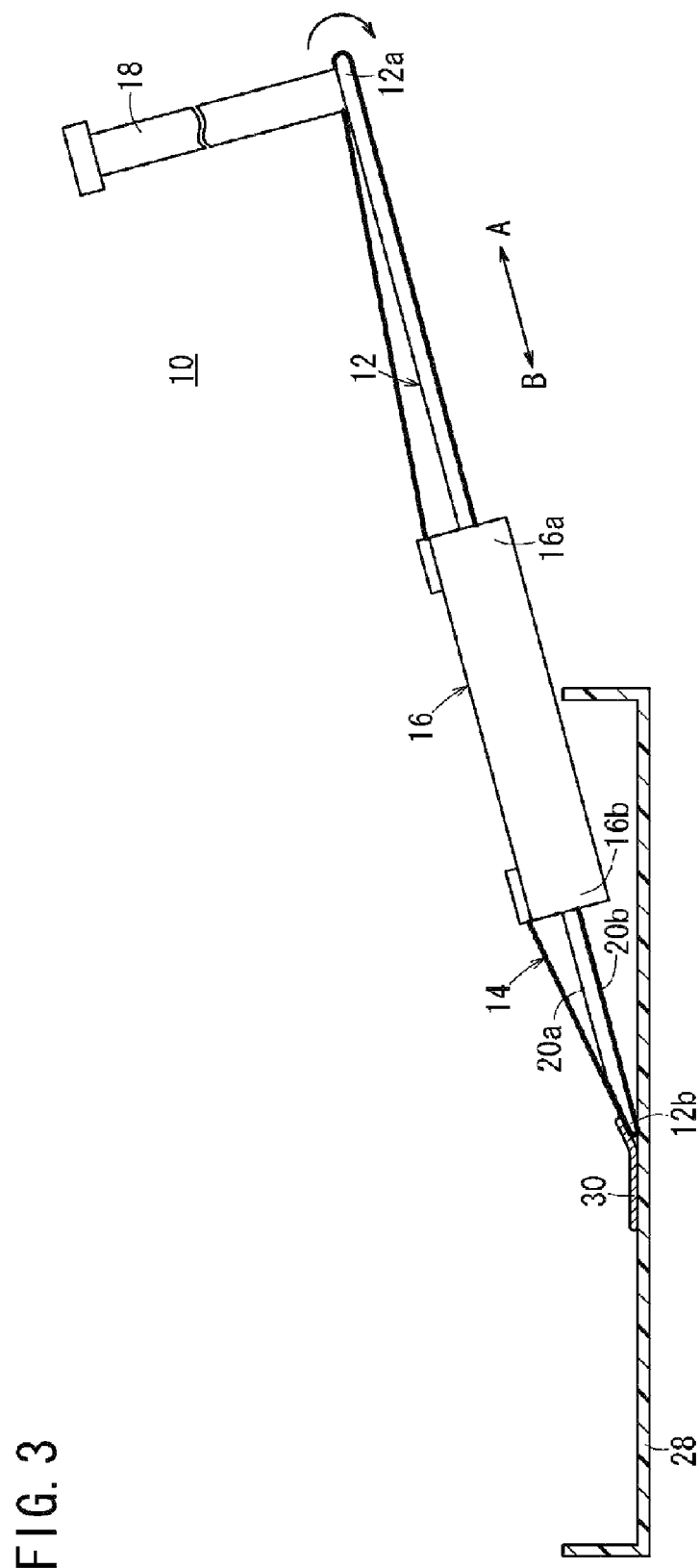
FIG. 3 illustrates the biological graft transferring instrument in operation with its forward end brought close to a sheet-shaped cell culture.

As shown in FIG. 3, the first step for operation is to prepare the culture dish 28 in which the sheet-shaped cell culture 30 has been cultivated. The operator holds the biological graft transferring instrument 10 in such a way as to incline it by a prescribed angle, with its forward end 12b downward (the direction indicated by the arrow B) and its base end 12a upward (the direction indicated by the arrow A), and then moves it so that the forward end 12b approaches the sheet-shaped cell culture 30. At this moment, the supporting member 12 and the belt-shaped member 14 project from the holding member 16 more toward the base end 12a than toward the forward end 12b. In other words, the holding member 16 is shifted toward the forward end 12b (the direction indicated by the arrow B) along the lengthwise direction from the center of the supporting member 12. More specifically, the operator holds the holding member 16 with one hand and the operation section 18 with the other hand. With the holding member 16 and the operation section 18 held in this way, and operator positions the forward end 12b of the instrument 10 to approach to the cell culture 30, the operator effects relative movement between the operation section and the holding member 16 so that the operation section 18 comes close relative to the holding member 16, and vice versa, to decrease to the distance between the holding member 16 and the operation section 18.

With the forward end 12b of the holding member 12 positioned between the sheet-shaped cell culture 30 and the surface of the culture dish 28 as shown in FIG. 3, the operator holds the holding member 16 and the operation section 18, and effects movement of the operation section 18 toward the holding member 16 and the sheet-shaped cell culture 30. For example, the operator pushes the operation section 18 toward the holding member 16 and the sheet-shaped cell culture 30

(the direction indicated by the arrow B). This operation causes the supporting member 12 and the belt-shaped member 14 to gradually project more from the holding member 16 toward the sheet-shaped cell culture 30 (the direction indicated by the arrow B). As a result, the forward end 12b of the supporting member 12 peels the sheet-shaped cell culture 30 from the culture dish 28 and gradually advances underneath the sheet-shaped cell culture 30.

A detailed description of the movement follows. As the operation section 18 is pushed toward the sheet-shaped cell culture 30 (the direction indicated by the arrow B), the forward end 12b of the supporting member 12 advances in the direction B of the arrow such that it gradually moves away from the holding member 16. The forward end 12b of the supporting member 12 pushes out the belt-shaped member 14, thereby causing a portion of the belt-shaped member 14 to gradually turn from the back surface 20b of the supporting member 12 to the front surface 20a of the supporting member 12 around the forward end 12b of the supporting member 12. At the same time, the base end 12a of the supporting member 12 moves toward the holding member 16 (the direction indicated by the arrow B), thereby causing a portion of the belt-shaped member 14 to gradually turn from the front surface 20a of the supporting member 12 to the back surface 20b of the supporting member 12 around the base end 12a of the supporting member 12. As the instrument shifts from the position shown in FIG. 3 to the position shown in FIG. 4, the length of the belt-shaped member 14 facing the front surface 20a of the supporting member 20 and positioned between the holding member 16 and the dish 28 increases.

Figure 4:
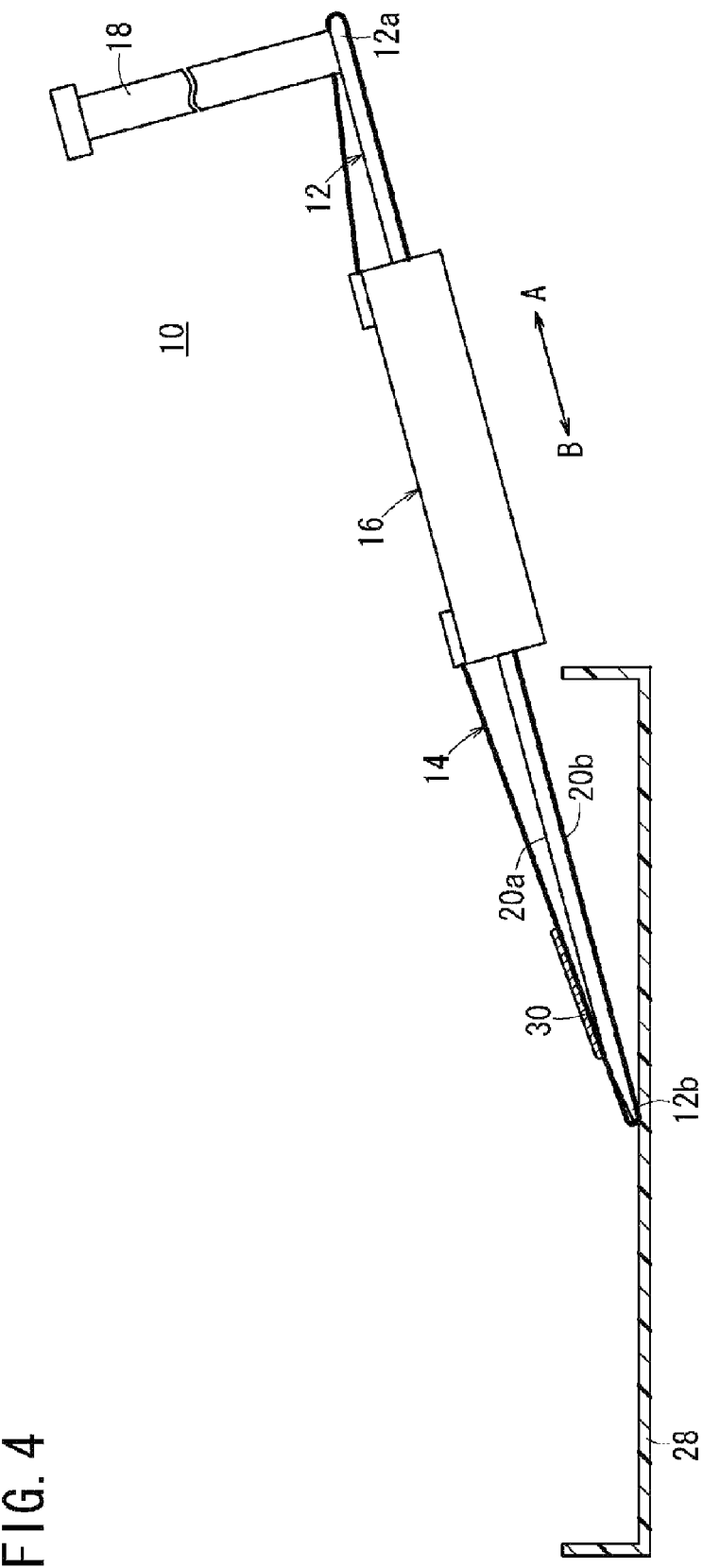
FIG. 4 illustrates the biological graft transferring instrument in operation as shown in FIG. 3, with its belt-shaped member carrying a sheet-shaped cell culture.

As a result, the supporting member 12 and the belt-shaped member 14 gradually move toward the forward end 12b (the direction indicated by the arrow B) relative to the holding member 16, and the forward end 12b of the biological graft transferring instrument 10 advances underneath the sheet-shaped cell culture 30, so that the sheet-shaped cell culture 30 is placed on the outer surface (holding surface) of the belt-shaped member 14 (See FIG. 4). The result is that the sheet-shaped cell culture 30 is held by firm adhesion on the outer surface of the sheet-shaped member 14 covering the front surface 20a of the supporting member 12, as shown in FIG. 4.

The sheet-shaped cell culture 30, which lies flat on the bottom of the culture dish 28, is gradually moved onto the outer surface of the belt-shaped member 14 while keeping its flat form and eventually supported on the supporting member 12, with the belt-shaped member 14 interposed between them.

Figure 5:
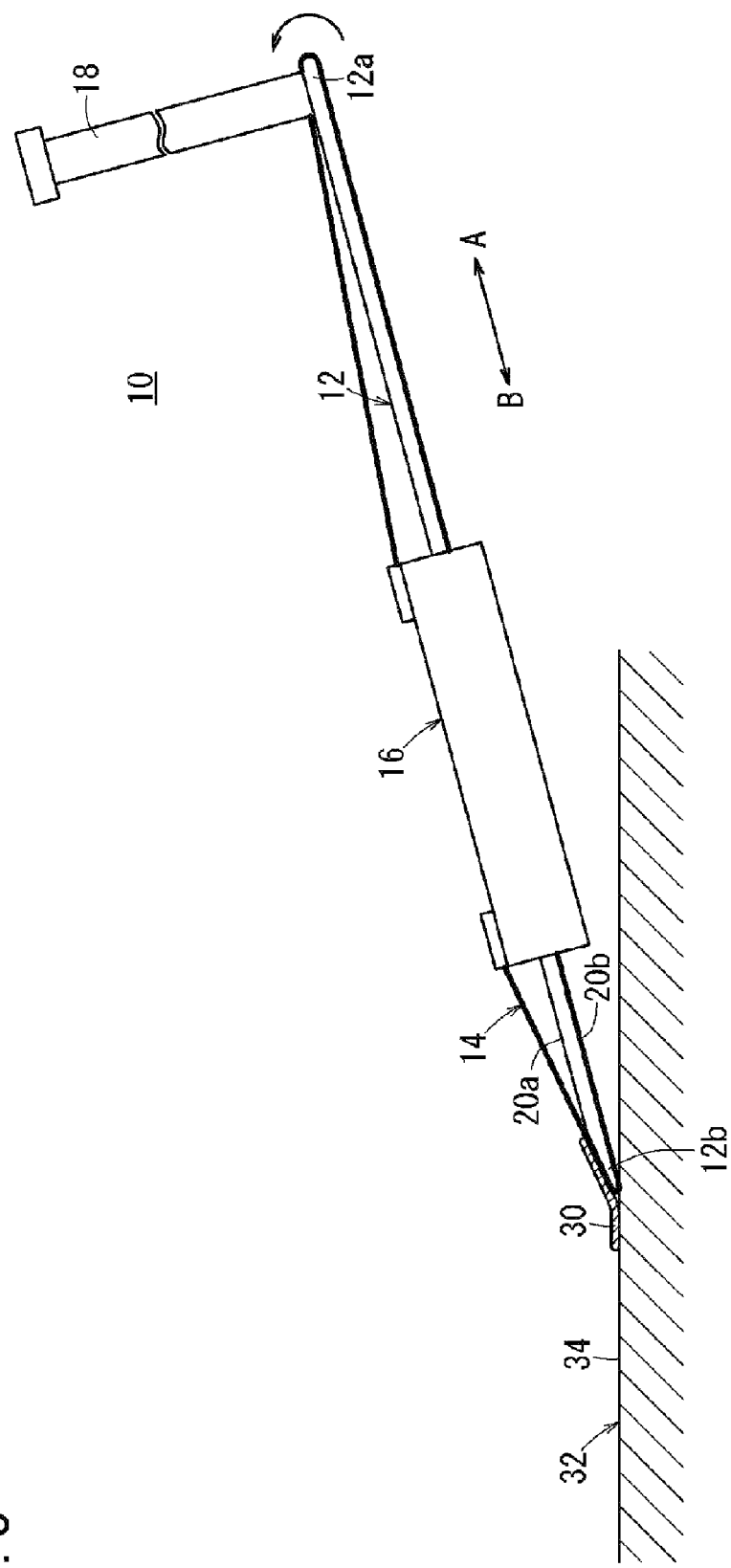
FIG. 5 illustrates the biological graft transferring instrument in operation in operation for transfer as shown in FIG. 4, with the sheet-shaped cell culture being transplanted to the patient's affected part.

After confirming that the sheet-shaped cell culture 30 has been completely placed on and held on the belt-shaped member 14 of the biological graft transferring instrument 10 as shown in FIG. 4, the operator moves the biological graft transferring instrument 10, together with the sheet-shaped cell culture 30, to the vicinity of the affected part 34 of the patient 32, as shown in FIG. 5. Then, the operator inclines the biological graft transferring instrument 10 again by a prescribed angle so that the forward end 12b of the instrument moves downward and comes near the affected part 34 to which the sheet-shaped cell culture 30 is to be transferred. To be more specific, the forward end 12b of the biological graft transferring instrument 10 is positioned such that it almost comes into contact with the surface of the affected part 34.

Next, as the operator holds the operation section 18 and the holding member 16, the operator slowly moves the operation section 18 relative to and away from the holding member 16 (the direction indicated by the arrow A), so that the base end 12a of the supporting member 12 is gradually shifted (in the direction indicated by the arrow A) away from the holding member 16. As a result, the belt-shaped member 14 under pressure by the base end 12a gradually turns around the base end 12a of the supporting member 12 from the back surface 20b of the supporting member 12 to the front surface 20a of the supporting member 12. At the same time, the forward end 12b of the supporting member 12 moves toward the holding member 16 (the direction indicated by the arrow A). As the result, the belt-shaped member 14 gradually turns around the forward end 12b from the front surface 20a of the supporting member 12 to the back surface 20b of the supporting member 12. In this way, the supporting member 12 and the belt-shaped member 14 gradually move toward the base end 12a (the direction indicated by the arrow A) relative to the holding member 16. Eventually, the forward end 12b of the biological graft transferring instrument 10 retracts, so that the sheet-shaped cell culture 30, which has been held on the belt-shaped member 14, is gradually transferred to the affected part 34. As the instrument shifts from the position shown in FIG. 4 to the position shown in FIG. 5, the length of the belt-shaped member 14 facing the front surface 20a of the supporting member 20 and positioned between the holding member 16 and the dish 28 decreases.

In other words, the sheet-shaped cell culture 30 keeps its position unchanged relative to the affected part 34 while the supporting member 12 and belt-shaped member 14 (which have held thereon the sheet-shaped cell culture 30) are gradually retracting. Finally, the sheet-shaped cell culture 30 is left on the affected part 34 as the supporting member 12 and belt-shaped member 14 approach being completely retracted or are completely retracted.

After the sheet-shaped cell culture 30 has been completely removed from the biological graft transferring instrument 10 and transferred (attached) to the affected part 34, the biological graft transferring instrument 10 is moved away from the affected part 34. The transfer of the sheet-shaped cell culture 30 to the affected part 34 of the patient 32 is thus completed.

According to the embodiment described above, the biological graft transferring instrument 10 is constructed of the plate-shaped supporting member 12, the belt-shaped member 14 extending in the lengthwise direction around the supporting member 12, and the holding member 16 to which are connected both ends of the belt-shaped member 14 which extends in the lengthwise direction around the supporting member 12, the holding member 16 being freely movable along the supporting member 12. Thus, the biological graft transferring instrument 10 permits the operator to take out the sheet-shaped cell culture 30 from the culture dish 28 and transfer the sheet-shaped cell culture 30, which has been taken out from the culture dish 28, to the affected part 34 of the patient 32. The biological graft transferring instrument 10 constructed as mentioned above is relatively small in size and economical to produce.

The biological graft transferring instrument 10 permits the operator to transfer the sheet-shaped cell culture 30 relatively certainly and securely by simply moving the supporting member 12 in the lengthwise direction with his hand holding the hand grip 16. Transfer in this way helps prevent the flat sheet-shaped cell culture 30 from changing in shape, sticking suitably to itself, and being damaged.

In addition, the biological graft transferring instrument 10 can pick up the sheet-shaped cell culture 30 floating in the culture dish containing water by means of its forward end inserted between the cell culture 30 and the culture dish 28. The sheet-shaped cell culture 30 is securely held and transferred by moving the supporting member 12.

Figure 6:
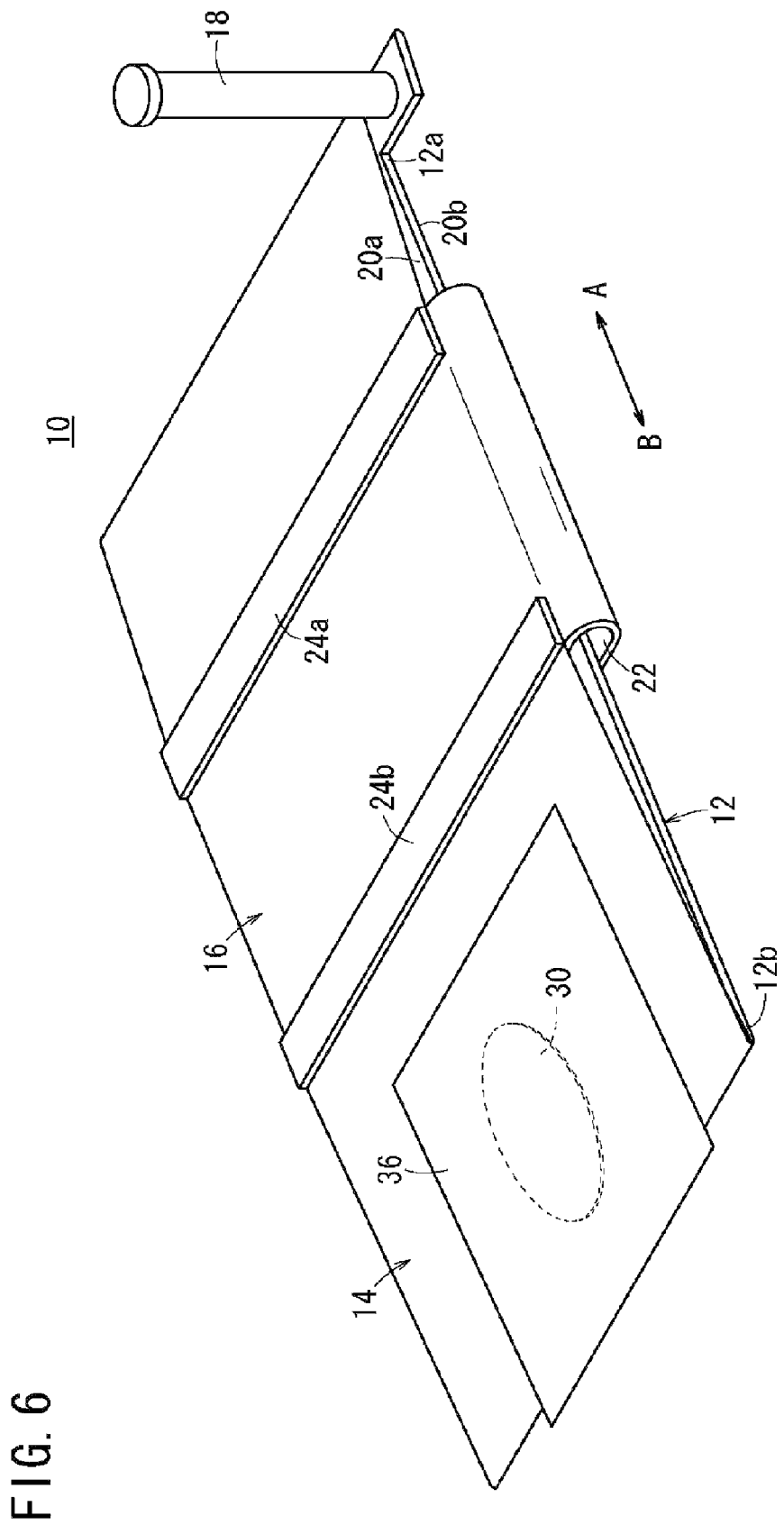
FIG. 6 is a perspective view of the biological graft transferring instrument during a transfer operation, with the sheet-shaped cell culture covered with a thin film.

Transfer of the sheet-shaped cell culture 30 to the affected part 34 of the patient 32 by means of the biological graft transferring instrument 10 may be accomplished by any other methods than mentioned above. For example, the sheet-shaped cell culture 30 may be covered with a thin film (or sheet) 36 during transfer as shown in FIGS. 6, 7A, and 7B.

According to this transfer method, the operator places the film 36 on the sheet-shaped cell culture 30 which has been placed on the belt-shaped member 14 of the biological graft transferring instrument 10, so that the sheet-shaped cell culture 30 is held between the film 36 and the belt-shaped member 14. In other words, the sheet-shaped cell culture and the film 36 are placed on the surface of the belt-shaped member 14. The number of the film 36 can be one or two, or could be more than two.

With the film 36 placed on the culture 30, the sheet-shaped cell culture 30 closely adheres to the film 36 by absorption with water to become stiff and temporarily increase in strength.

Then, the operator manipulates the biological graft transferring instrument 10 with the operation section 18 so that the forward end 12b of the supporting member 12 retracts. This action gradually transfers the sheet-shaped cell culture 30, together with the film 36, to the affected part 34, as shown in FIG. 7B. After confirming that the sheet-shaped cell culture 30 has completely left the biological graft transferring instrument 10 and transferred to the affected part 34, the operator gently removes the film 36 from the sheet-shaped cell culture 30. This final step completes the transplantation of the sheet-shaped cell culture 30 to the affected part 34 of the patient 34.

The foregoing method permits the sheet-shaped cell culture 30 to be transferred, together with the film 36 placed thereon, to the affected part 34 from the belt-shaped member 14. Transfer in this way prevents the sheet-shaped cell culture 30 from being caught by the forward end 12b of the supporting member 12. In addition, the fact that the sheet-shaped cell culture 30 is transferred to the affected part 34 together with the film 36 which is stiffer than the sheet-shaped cell culture 30 prevents suitably the sheet-shaped cell culture 30 from being damaged and ensures the stable and secure transfer of the sheet-shaped cell culture 30 to the affected part 34.

Another transfer method is as follows. The operator turns around (upside down) the biological graft transferring instrument 10, with the belt-shaped member 14 carrying the sheet-shaped cell culture 30. Then, the operator positions the biological graft transferring instrument 10 such that the sheet-shaped cell culture 30 faces the affected part 34 of the patient 32. The operator brings the biological graft transferring instrument 10 close to the affected part 34 so that the sheet-shaped ell culture 30 comes into direct contact with the affected part 34. The operator presses the sheet-shaped cell culture 30 against the affected part 34 by means of the biological graft transferring instrument 10. The operator moves the biological graft transferring instrument 10 in the horizontal direction so that it leaves away from the affected part 34. Thus, the sheet-shaped cell culture 30 can leave the belt-shaped member 14 while allowing the sheet-shaped cell culture 30 to remain on the affected part 34. In this way, the implantation of the sheet-shaped cell culture 30 to the affected part 34 is completed simply and securely.

The method of operation mentioned above makes it possible for the operator to implant the sheet-shaped cell culture 30 simply and securely to the affected part 34 of the patient 32 without manipulating the operation section 18.

Figure 8:
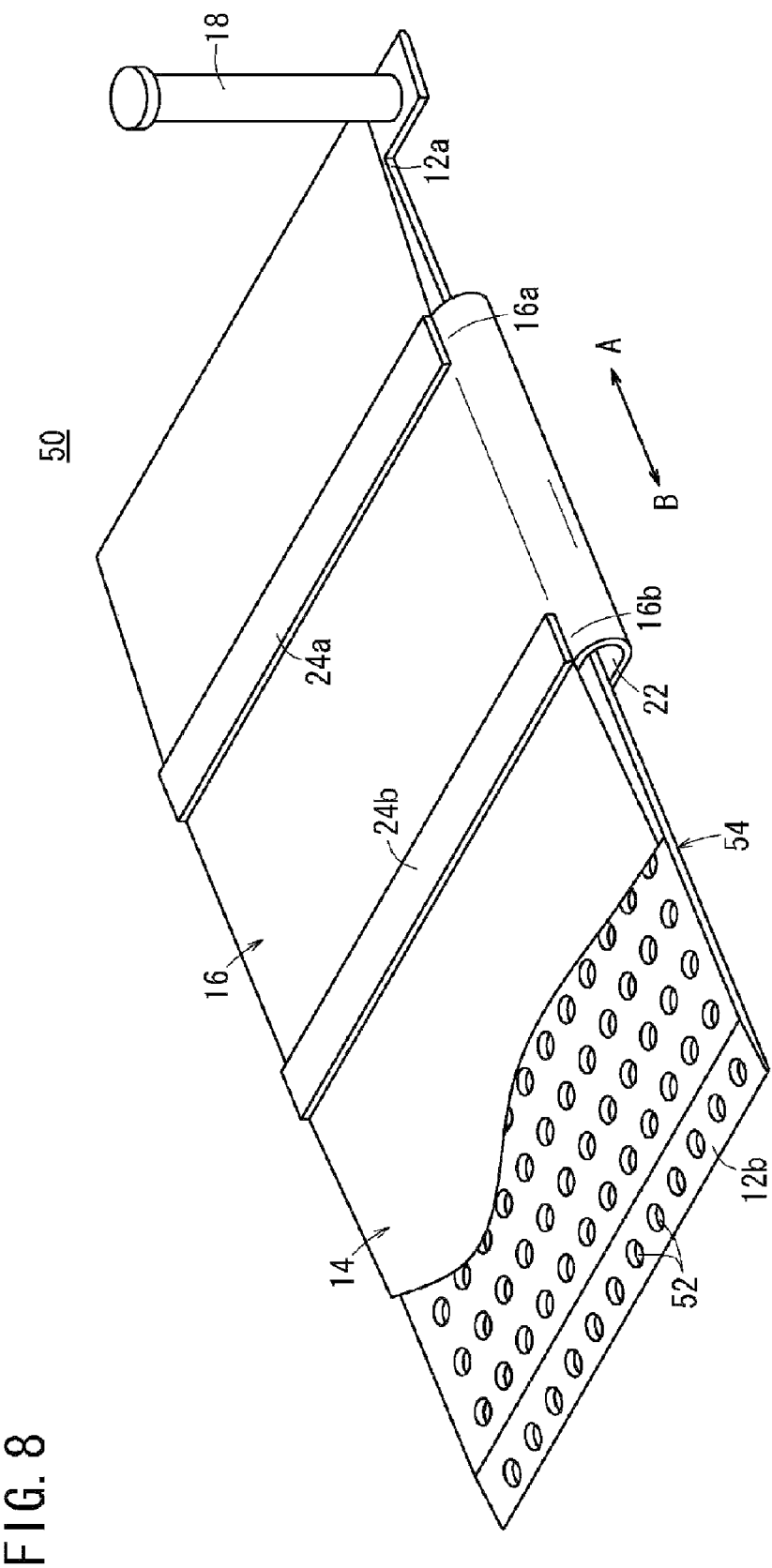
FIG. 8 is a partly cut-away perspective view of the biological graft transferring instrument having a supporting member with a plurality of holes according to one modified embodiment disclosed by way of example.
Figure 9:
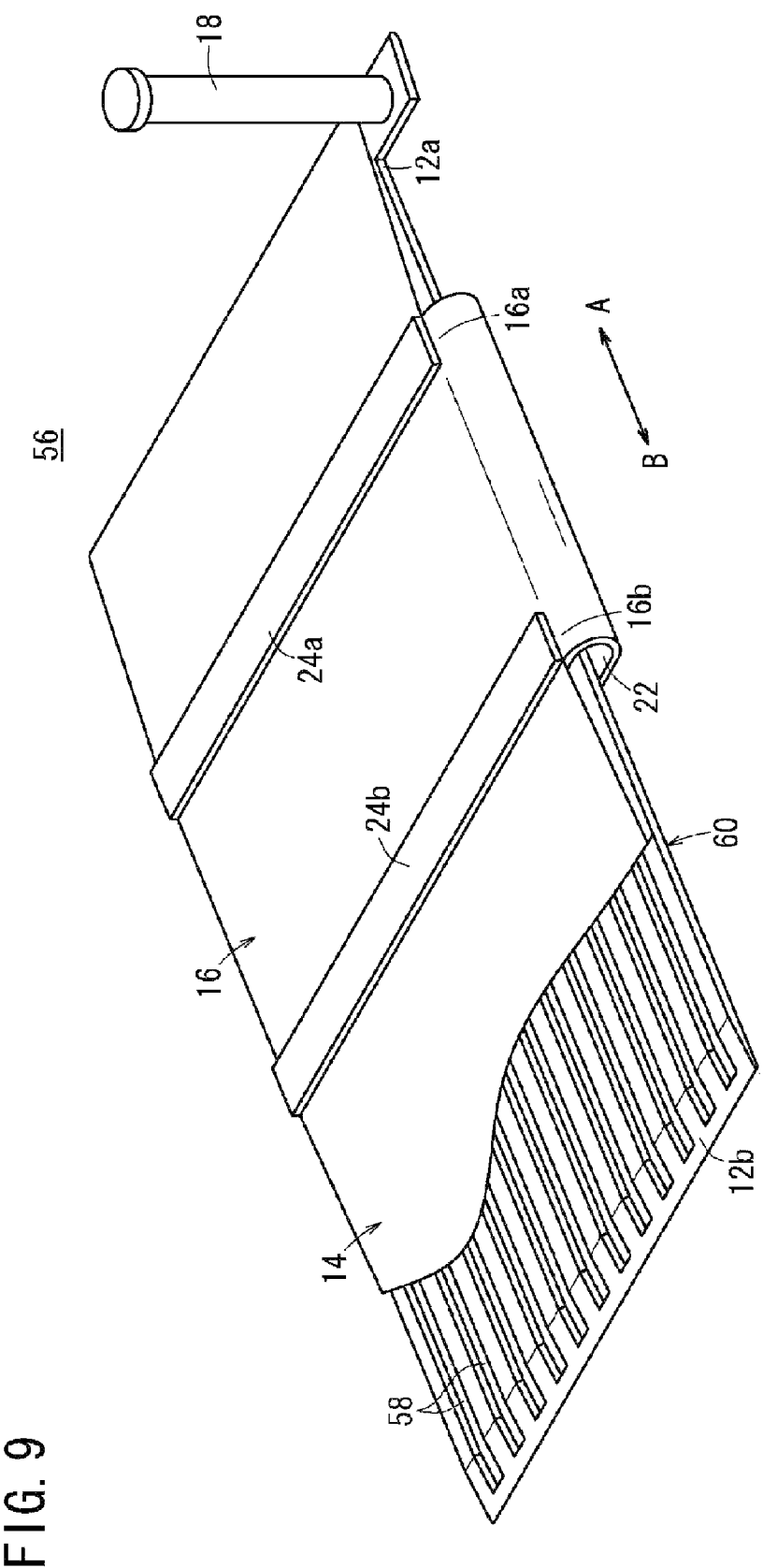
FIG. 9 is a partly cut-away perspective view of the biological graft transferring instrument having a supporting member with a plurality of slit holes according to another modified embodiment disclosed by way of example.
Figure 10:
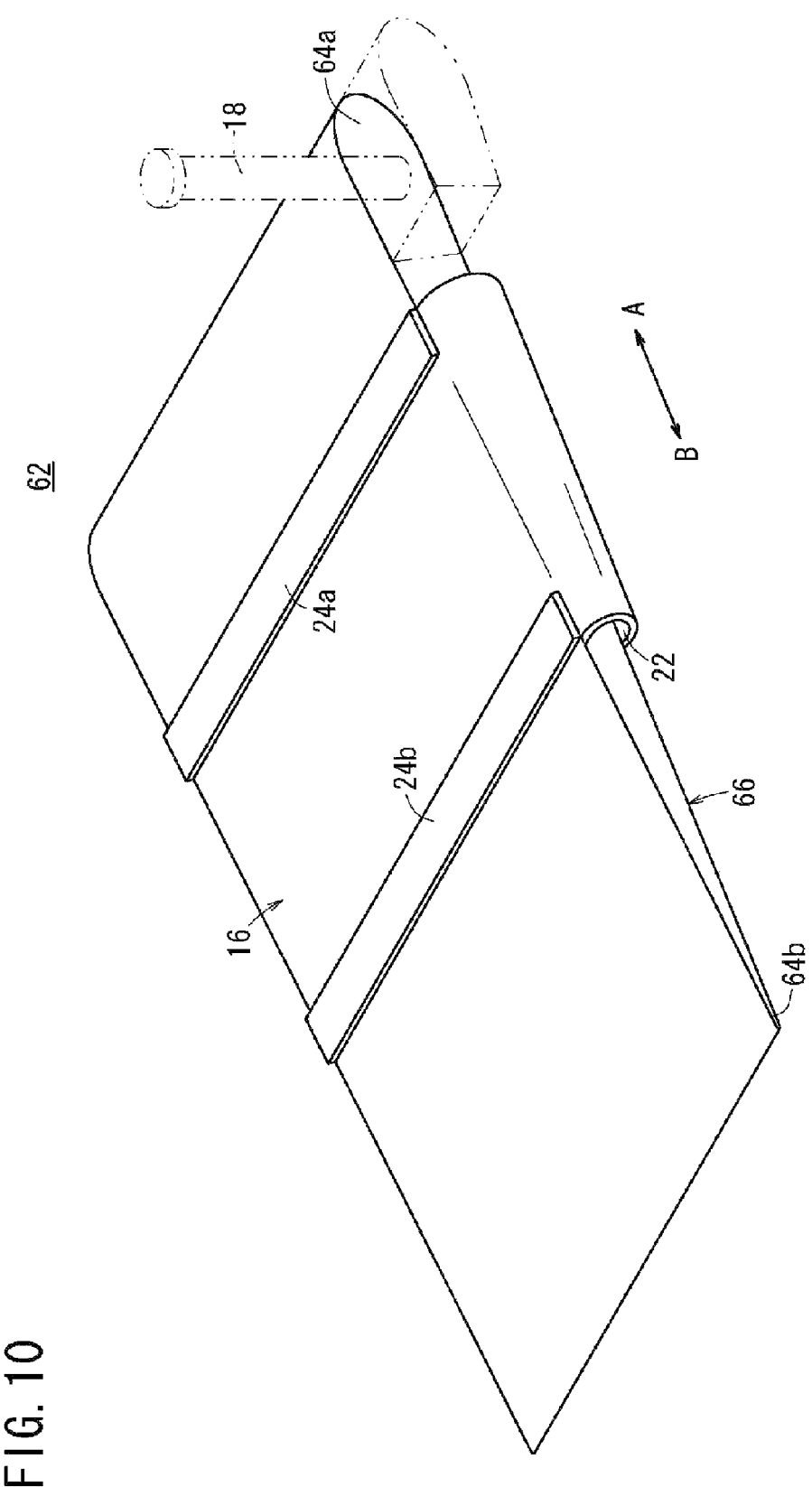
FIG. 10 is a partly cut-away perspective view of the biological graft transferring instrument having a supporting member which gradually increases in thickness toward the base end according to a third modified embodiment disclosed by way of example.

There has been demonstrated so far the biological graft transferring instrument 10 which has the supporting member 12 in the form of approximately rectangular plate of uniform thickness. However, the instrument and method are not limited in this regard. One modified form of the biological graft transferring instrument is shown in FIG. 8. Here, the biological graft transferring instrument 50 includes the supporting member 54 with a plurality of holes 52 positioned at regular intervals. The biological graft transferring instrument 56 shown in FIG. 9 is another modified form of the instrument. In this embodiment, the supporting member 60 has a plurality of parallel spaced slit holes 58 extending in the lengthwise direction (in the directions indicated by arrows A and B). The biological graft transferring instrument 62 shown in FIG. 10 illustrates a further modification in which the supporting member 66 is configured to gradually increase in thickness, in the direction indicated by the arrow A, from the forward end 64b to the base end 64a with an arc cross-section. That is, the base end 64a is arc-shaped or arcuate as shown in FIG. 10.

The supporting members 54, 60, 66 mentioned above are not specifically restricted in shape so long as they are constructed such that the belt-shaped member 14 extending around the front surface 20a and the back surface 20b of the supporting members generally smoothly turns as they are displaced. For example, the supporting members 54 and 60 shown in FIGS. 8 and 9, which have respectively the holes 52 and the slit holes 58, permit the belt-shaped member 14 to reduce frictional resistance upon turning along the supporting members 54 and 60. Likewise, the supporting member 66 shown in FIG. 10 also permits the belt-shaped member 14 to generally smoothly turn because its base end 64a has an arc-shaped cross-section which reduces frictional resistance.

The biological graft transferring instrument 10 described above uses the belt-shaped member 14 with a flat smooth surface. However, the instrument is not limited in this regard. For example, as shown in FIG. 11A, the biological graft transferring instrument 68 can have a belt-shaped member 72 with projections 70 of a certain height on its outer surface.

These projections 70 are provided at regular intervals in the lengthwise direction of the belt-shaped member 72, and they are arranged generally along the center line crossing the widthwise direction. The supporting member 12 is moved so that the projections 70 are positioned at the forward end 12b of the supporting member 12. Then, with the forward end 12b inserted under the sheet-shaped cell culture 30, the operator moves the operation section 18 toward (in the direction of the arrow B) the holding member 16. This movement causes the projections 70, which have been inserted underneath the sheet-shaped cell culture 30, to rise upward and hold and stick into the sheet-shaped cell culture 30.

As the result, the sheet-shaped cell culture 30, which has been stuck by the projections 70, is mounted on the outer surface of the belt-shaped member 72 inserted under the sheet-shaped cell culture 30. In other words, this modification permits the sheet-shaped cell culture 30 to be relatively securely and stably held on the belt-shaped member 72 owing to the projections 70 which stick into the sheet-shaped cell culture 30.

Figure 11B:
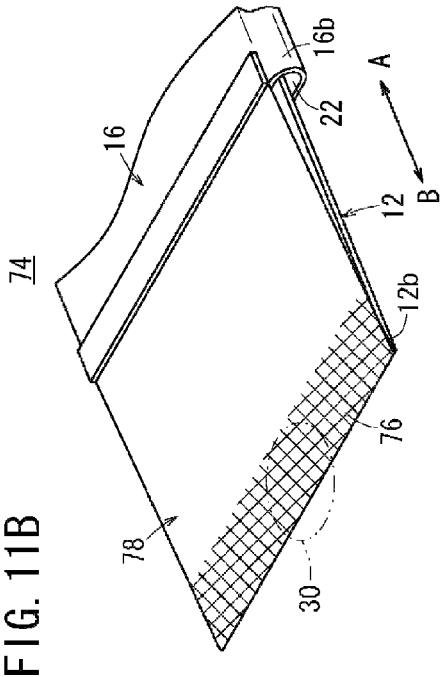
FIGS. 11A-11D are enlarged cross-sectional views of the biological graft transferring instrument with a belt-shaped member according to fourth to seventh embodiments disclosed by way of example.
Figure 11D:
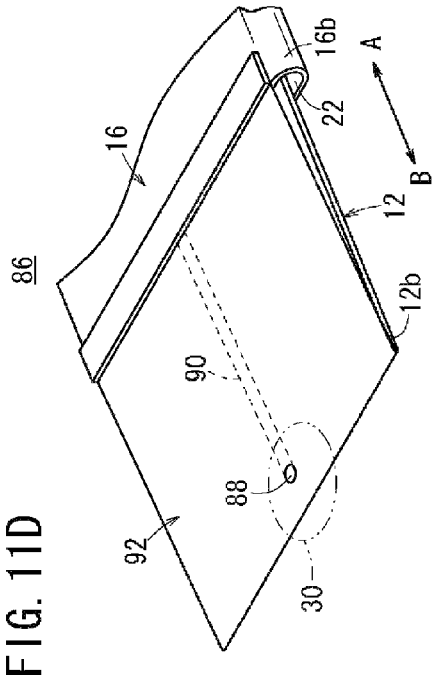
Figure 11A:
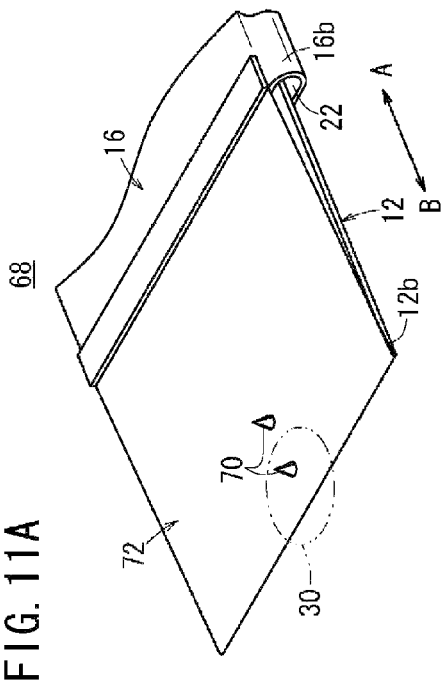
Figure 11C:
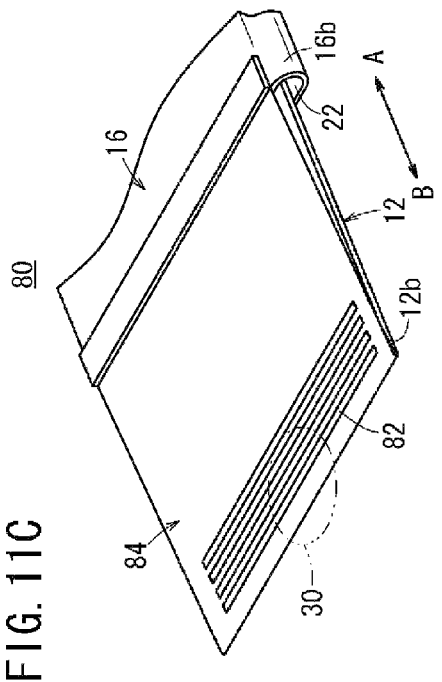

FIG. 11B shows the biological graft transferring instrument 74 according to a fifth modification. Here, the belt-shaped member 78 is provided with the resisting part 76, which is a rough-surfaced portion of the outer surface of the belt-shaped member 78. FIG. 11C shows the biological graft transferring instrument 80 according to a sixth modification in which the belt-shaped member 84 is provided with a plurality of grooves 82, which extend at right angles to the lengthwise direction (right angle to the direction indicated by the arrows A and B) on the outer surface of the belt-shaped member 84. FIG. 11D shows the biological graft transferring instrument 86 according to a further modification. According to this modification, the outer surface of the belt-shaped member 92 is provided with the sucking hole 88. Incidentally, the sucking hole 88 communicates with the passage 90 extending in the lengthwise direction of the belt-shaped member 92.

When inserted underneath the sheet-shaped cell culture 30, the rough-surfaced resisting part 76 or the grooves 82 permit the belt-shaped member 78, 84 to relatively securely and stably contact and hold the sheet-shaped cell culture 30 on the members 78, 84 by means of the resisting action to the rough-surfaced resisting part 76 and the grooves 82. Likewise, when inserting the belt-shaped member 92 to place the sucking hole 88 underneath the sheet-shaped cell culture 30, the sucking hole 88 permits the belt-shaped member 92 to securely and stably place and hold the sheet-shaped cell culture 30 thereon owing to absorption of the sheet-shaped cell culture 30 by means of suction force which is produced as it sucks fluid including water.

Figure 12:
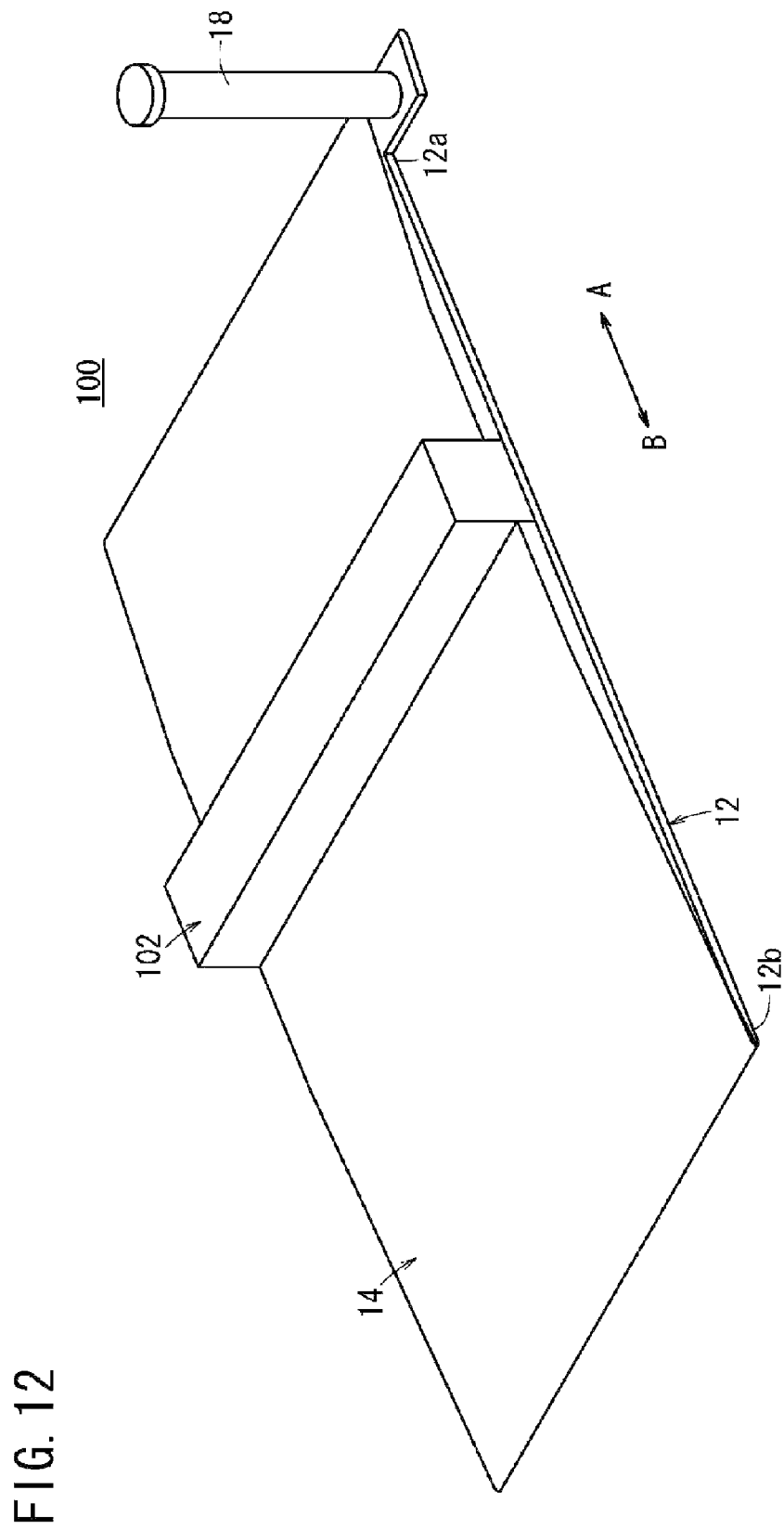
FIG. 12 is a perspective view of the biological graft transferring instrument having a holding member in the form of a rectangular parallelepiped according to an eighth example disclosed by way of example.
Figure 13:
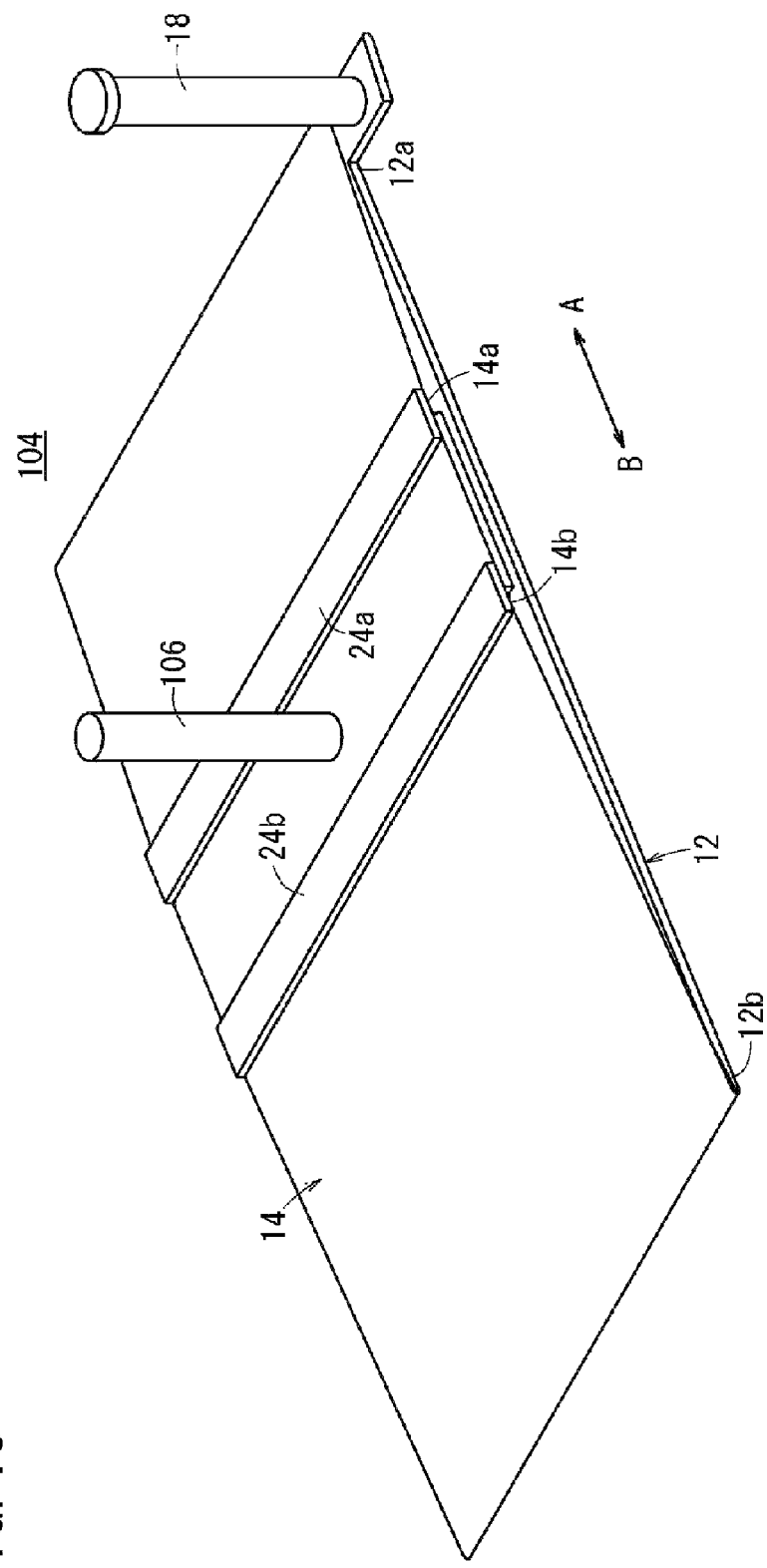
FIG. 13 is a perspective view of the biological graft transferring instrument having a holding member in the form of a circular cylinder according to a ninth embodiment disclosed by way of example.

The biological graft transferring instrument 10 described above includes the holding member 16 constructed as a hollow rectangular cross sectional case having the opening hole 22 at its center. However, the instrument is not limited in this regard and may be modified, by way of example, as follows. For example, the biological graft transferring instrument 100 shown in FIG. 12, constituting an eighth modification of the instrument, has the holding member 102 in the form of rectangular parallelepiped having a predetermined height extending upward. The biological graft transferring instrument 104 shown in FIG. 13 as a ninth modification has the holding member 106 in the form of circular cylinder extending upward. The holding member 102 or 106 can improve the operability for transferring the sheet-shaped cell culture 30.

Figure 14:
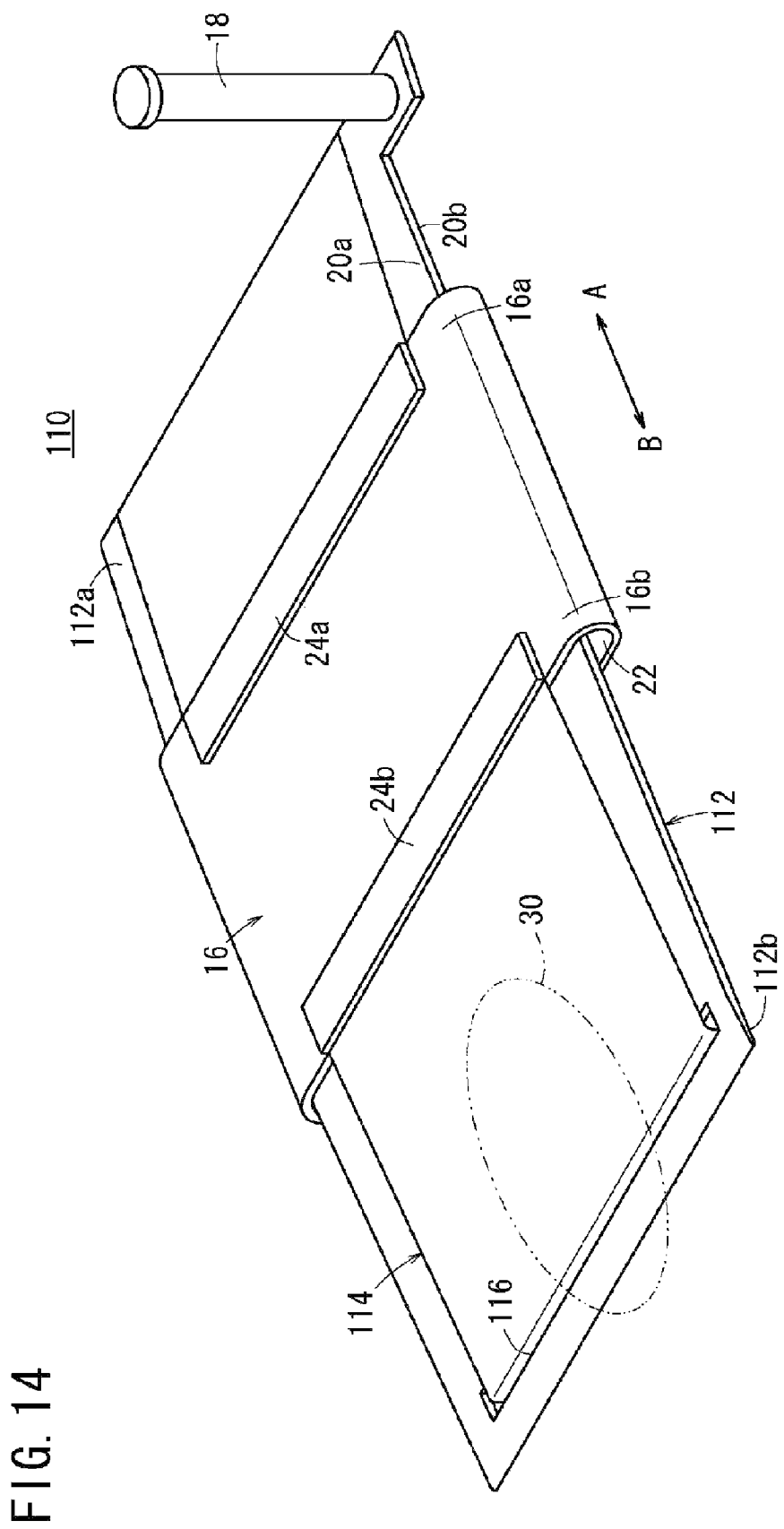
FIG. 14 is a perspective view of the biological graft transferring instrument having a holding member according to a tenth embodiment disclosed by way of example, with the instrument having a belt-passing slit near the forward end of the supporting member.

The biological graft transferring instrument 110 shown in FIGS. 14 and 15A represents a tenth modification in which the supporting member 112 in which there is formed, near the forward end 112b of the supporting member 112, the belt passing slit 116 which permits the belt-shaped member 114 to pass through. The belt passing slit 116 is a predetermined distance (a little) away from the forward end 112b of the supporting member 112 toward the base end 112a (in the direction of the arrow A), and it extends straight in the widthwise direction of the supporting member 112, but is shorter than the width of the supporting member 112. In other words, it is formed such that both ends of the belt passing slit 116 are a little inside from both sides of the supporting member 112. Meanwhile, the belt-shaped member 114 is approximately equal to or slightly shorter than the width of the belt-passing slit 116.

The belt-shaped member 114 passes through the belt passing slit 116 of the supporting member 112 and extends around (is wound around) the belt passing slit 116 and the base end 112a. In other words, the belt-shaped member 114 does not cover the forward end 112b of the supporting member 112 but passes through the belt passing slit 116 near the forward end 112a of the supporting member 112 and covers the supporting member 112.

The biological graft transferring instrument 110 offers the advantage of inhibiting or preventing the sheet-shaped cell culture 30 closely adhering to the belt-shaped member 114 from being caught, together with the belt-shaped member 114, to the back surface 20b of the supporting member 112 when the operator manipulates the operation section 18 to transfer the sheet-shaped cell culture 30.

In other words, when the operator manipulates the operation section 18 to slowly retract the belt-shaped member 114, the belt-shaped member 114 does not reach the forward end 112b of the supporting member 112 but turns back around the belt passing slit 116, which is formed away from the forward end 112b toward the base end 112a. In this way only the sheet-shaped cell culture 30 is moved to the forward end 112b and then transferred to the affected part 34 of the patient 32.

Since the belt-shaped member 114 is not wound around the forward end 112b of the supporting member 112 and the belt passing slit 116 (for the belt-shaped member 114 to pass through) is formed relatively narrow in the lengthwise direction (or in the directions of the arrows A, B) of the supporting member 112, the sheet-shaped cell culture 30 is inhibited or prevented from moving to the back surface 20b of the supporting member 112 through the belt passing slit 116.

The biological graft transferring instrument 120 shown in FIG. 15B has the supporting member 122 in which is formed the belt passing slit 124 (for the belt-shaped member 114 to pass through) spaced from the forward end 112b of the supporting member 122 toward the base end 122a (in the direction of the arrow A) at a predetermined distance, with the forward end 122b of the supporting member 122 offset downward. That is, the supporting member 122 has its forward end 112b formed with a step.

The biological graft transferring instrument 122, which is used for the transfer of the sheet-shaped cell culture 30 with the above-mentioned supporting member 122, causes the belt-shaped member 114 and the supporting member 122 to retract so that the sheet-shaped cell culture 30 moves downward along the offset forward end 122b. In this way, the sheet-shaped cell culture 30 leaves from the forward end 122b and suitably transfers to the affected part 34 of the patient 32. During this operation, the sheet-shaped cell culture 30 moves to the offset forward end 122b of the supporting member 122 so that it surely leaves from the belt-shaped ember 114. This causes the sheet-shaped cell culture 30 to surely transfer to the affected part 34 of the patient 32 from the belt-shaped member 114. In this regard, it becomes possible to escape the sheet-shaped cell culture 30 from the belt-shaped member 114 more securely and transfer the sheet-shaped cell culture 30 to the affected part 34 of the patient 32.

Figure 16:
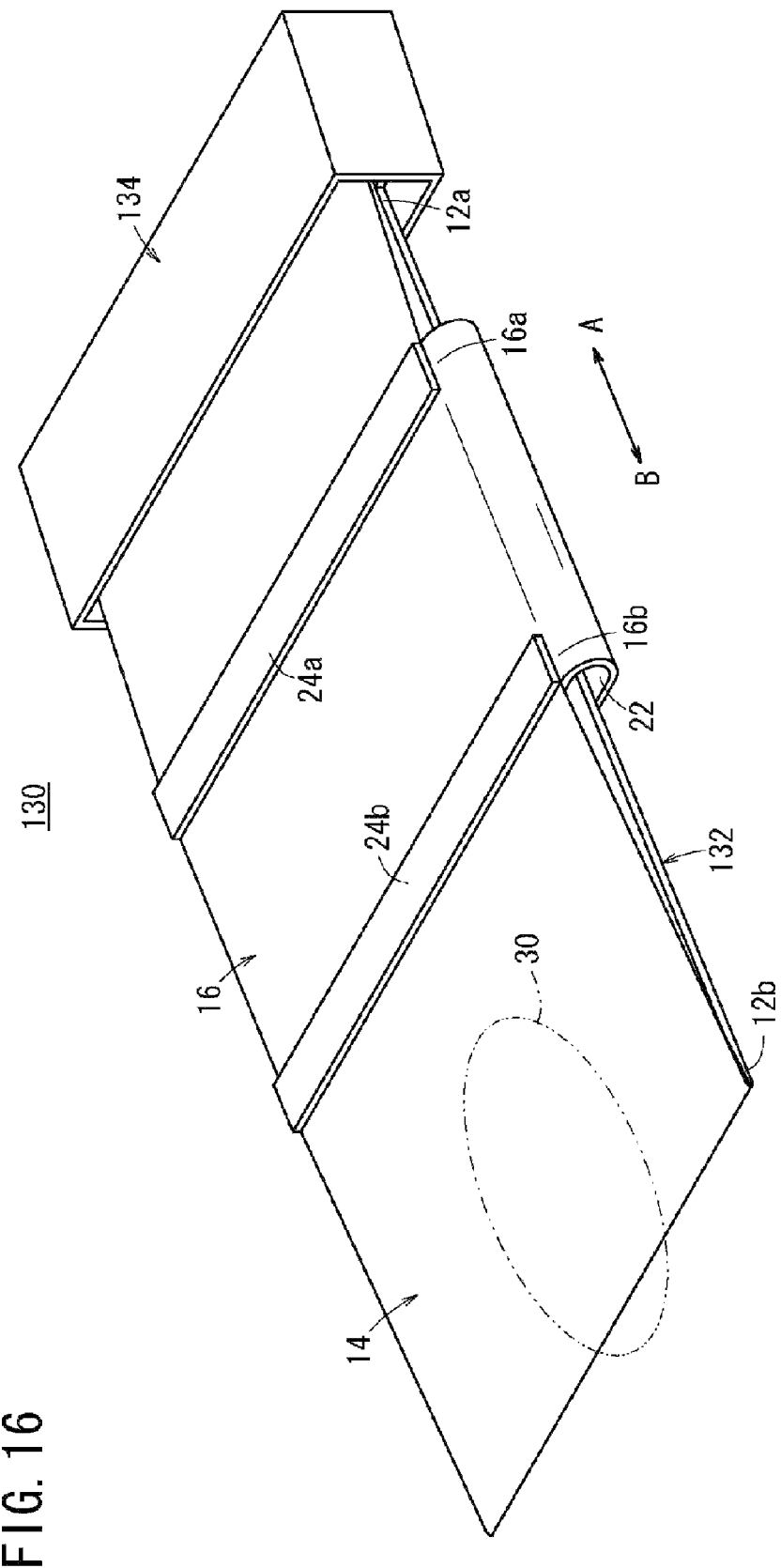
FIG. 16 is a perspective view of the biological graft transferring instrument according to an eleventh embodiment disclosed by way of example, wherein the instrument has a box-shaped operation section at the base end of the supporting member.
Figure 17:
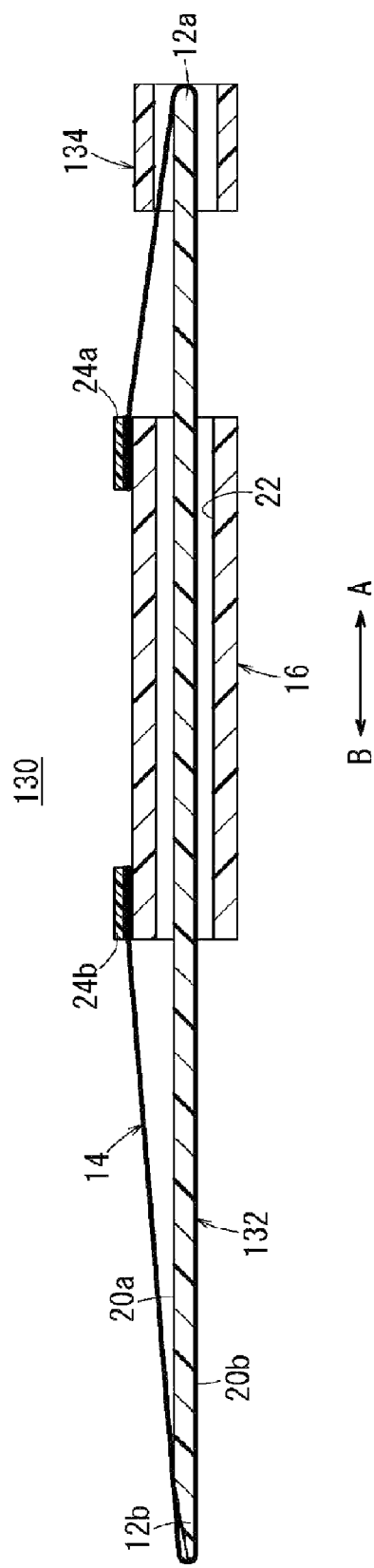
FIG. 17 is a longitudinal cross-sectional view of the biological graft transferring instrument shown in FIG. 16.

The biological graft transferring instrument 130 shown in FIGS. 16 and 17 according to an eleventh modification includes the operation section 134 (resembling a three-dimensional box shape) attached to the base end 12a of the supporting member 132. This operation section 134 has a hollow rectangular cross section, so that it permits the base end 12a of the supporting member 132 to pass through its hollow part and both lateral sides of the base end 12a join to the inner walls of the operation section 134. In other words, the operation section 134 is formed integrally with the base end 12a of the supporting member 132. In addition, the operation section 134 has its upper and lower surfaces formed flat horizontally.

In order to manipulate the biological graft transferring instrument 130 to transfer the sheet-shaped cell culture 30, the operator moves the operation section 134 while holding the holding member 16 such that the holding member 16 moved closer towards or farther away from the operation section 134 (in the A or B direction), thereby moving integrally the supporting member 132 joined to the operation section 134. As a result, the top and bottom surface which the operator grips are formed flat, and gripping the operation section 134 having a predetermined width in the widthwise direction of the supporting member 132 facilitates stable operation. This improves the operability of the biological graft transferring instrument 130.

Alternatively, it is also possible to move the holding member (main body) 16 back and forth relative to the operation section 134. In other words, the operator may move the holding member 16 back and forth while keeping the operation section 134 stationary. In this way, the operator is able to mount the sheet-shaped ell culture 30 onto the belt-shaped member 14 or to transfer the sheet-shaped cell culture 30 from the sheet-shaped member 14 while keeping constant the distance from the operation section 134 on hand to the forward end 12b of the supporting member (displacement member) 132.

Figure 18:
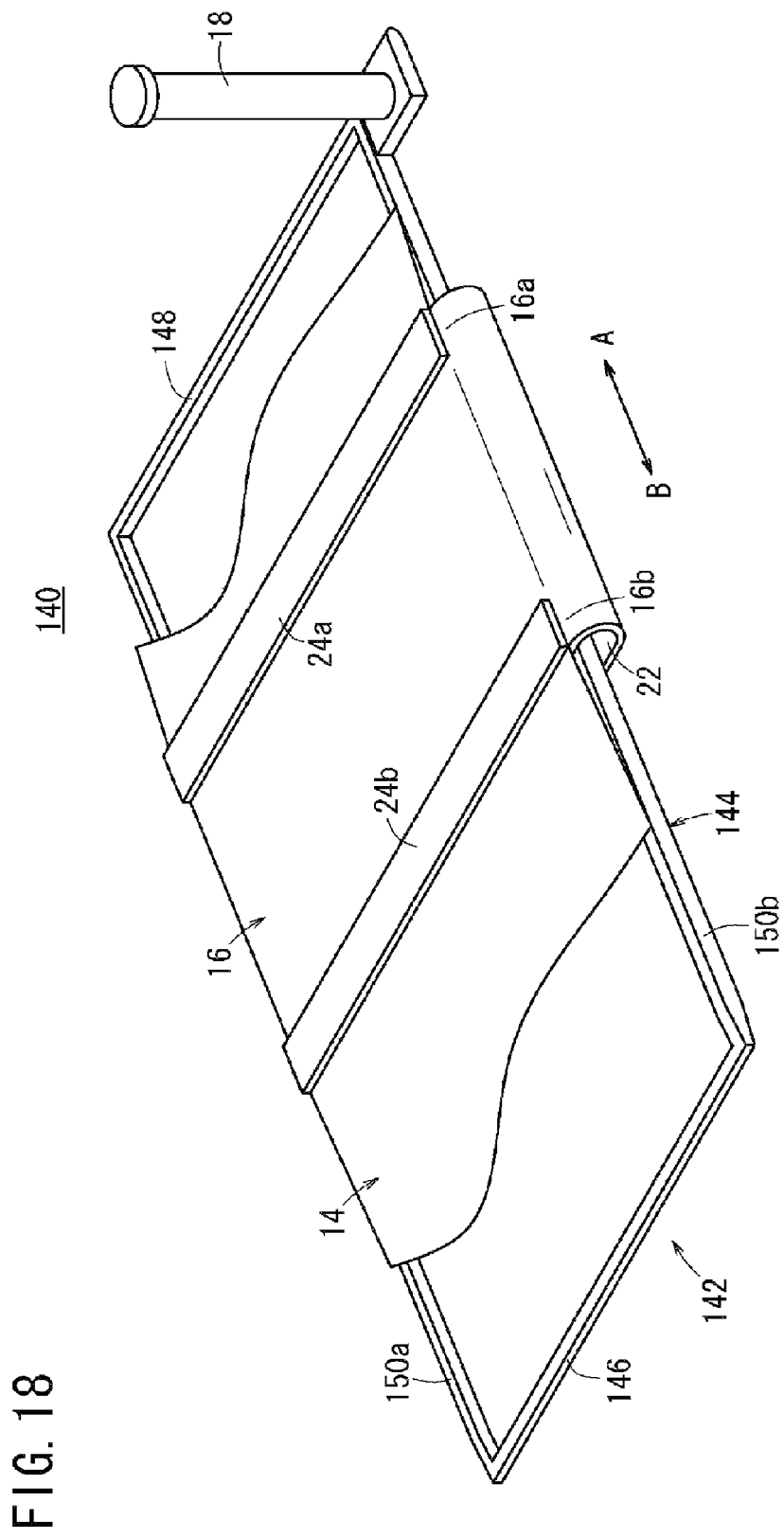
FIG. 18 is a perspective view of the biological graft transferring instrument according to a twelfth embodiment disclosed by way of example, wherein the instrument has a frame-shaped supporting member.

The biological graft transferring instrument 140 shown in FIG. 18 represents a twelfth modification in which the supporting member 142 constructed as a hollow frame 144. This frame 144 has an approximately rectangular shape composed of the forward frame 146 constituting the forward end of the supporting member 142, the base frame 148 constituting the base end of the supporting member 142, and the paired side frames 150a, 150b joining together the forward and base ends of the forward frame 146 and the base frame 148. The belt-shaped member 14 is wound around the forward frame 146 and the base frame 148. The supporting member 142 is constructed to have the frame 144 including four of each frame, e.g., the forward frame 146, the base frame 148, and two side frames 150a, 150b that are disposed on the outer edge.

The supporting member 142 constructed as mentioned above helps prevent the belt-shaped member 14 (wetted with water) from sticking to the front and back surfaces of the supporting member 142 while the biological graft transferring instrument 140 is transferring the sheet-shaped cell culture 30. Thus, even in the case where the supporting member 142 and the belt-shaped member 14 are wetted with water, the belt-shaped member 14 does not stick to the supporting member 142 but relatively smoothly moves around it while the inner surface of the belt-shaped member 14 keeps contact with the forward frame 146 and the base frame 148 of the supporting member 142, thereby permitting the transfer of the sheet-shaped cell culture 30.

Figure 19:
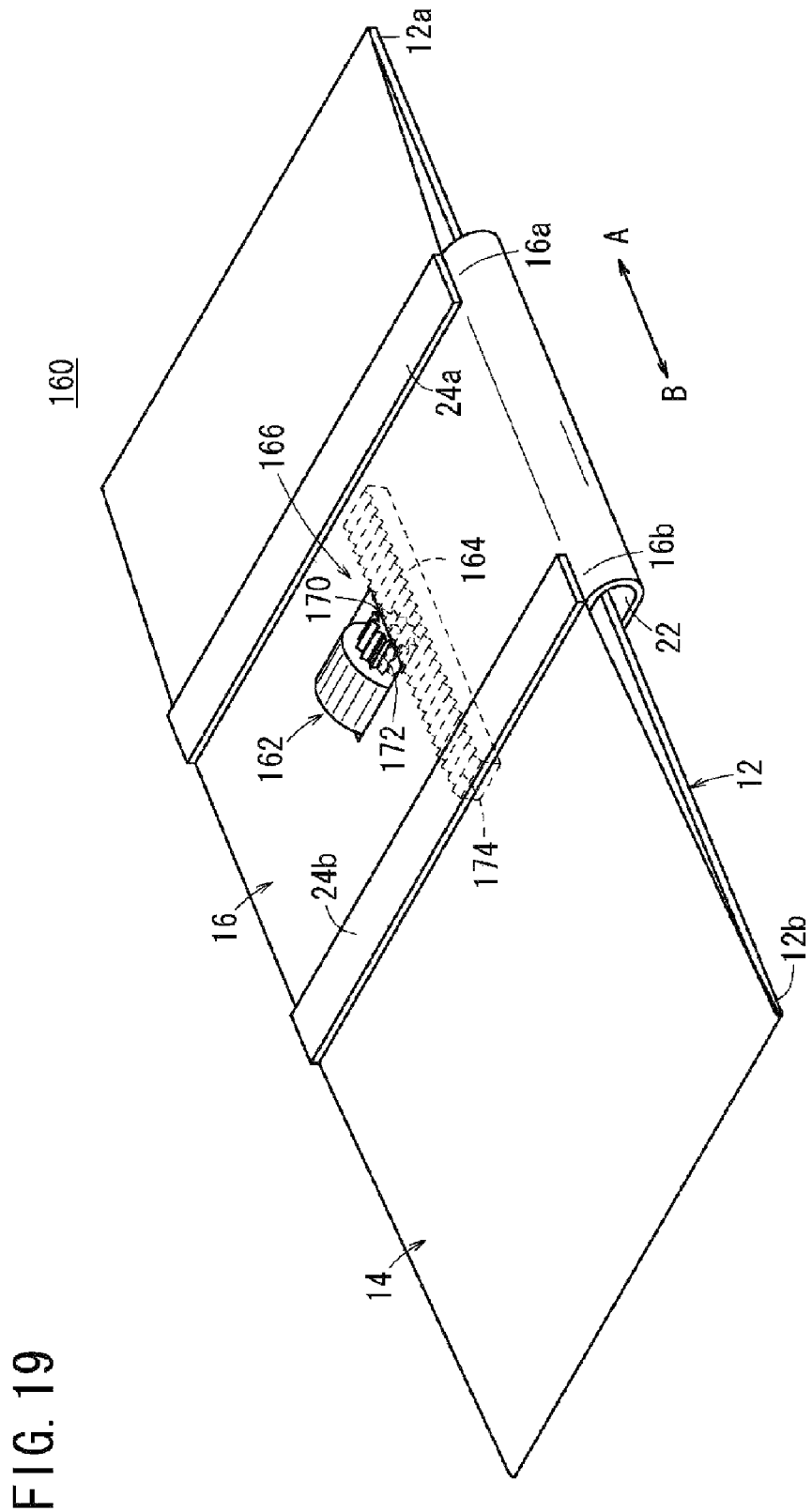
FIG. 19 is a perspective view of the biological graft transferring instrument according to a thirteenth embodiment disclosed by way of example, the instrument having a mechanism for forward and backward movement.
Figure 20A:
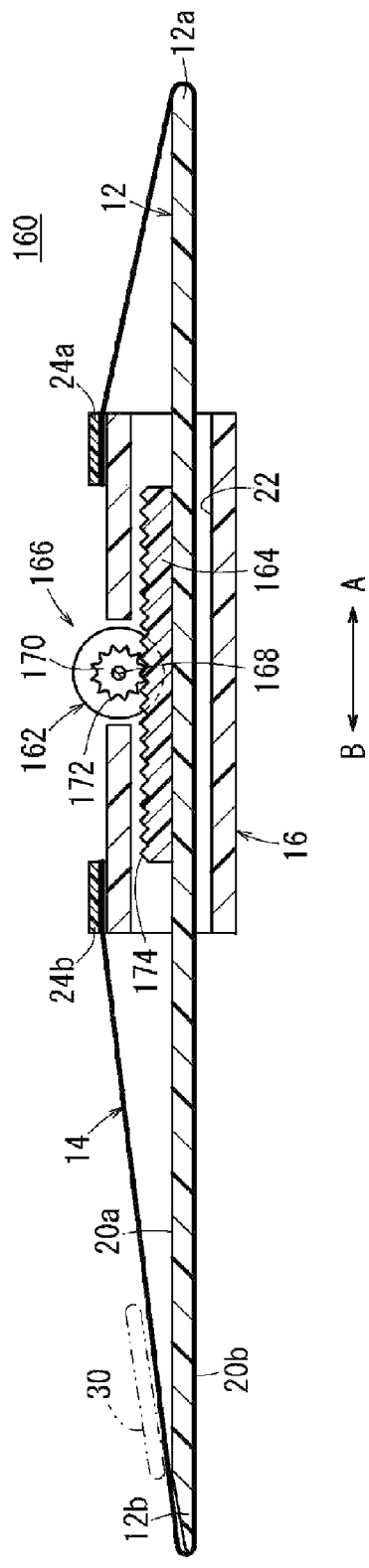
FIG. 20A is a longitudinal cross-sectional view of the biological graft transferring instrument shown in FIG. 19.
Figure 20B:
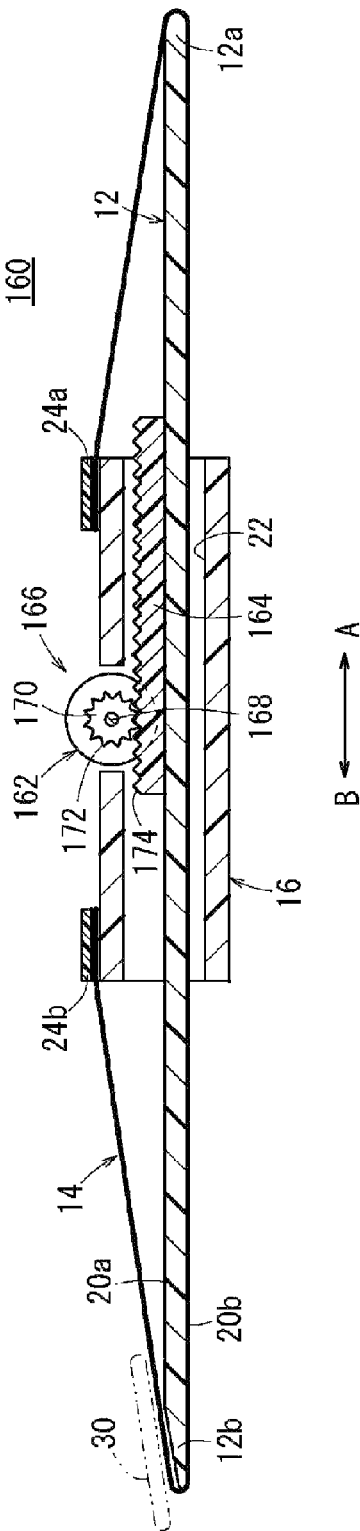
FIG. 20B is a longitudinal cross-sectional view of the biological graft transferring instrument shown in FIG. 20A, the instrument moving the belt-shaped member by way of the mechanism for forward and backward movement.

The biological graft transferring instrument 160 shown in FIGS. 19, 20A and 20B represent a thirteenth modification that includes a back and forth mechanism 166 for moving the supporting member 12 back and forth. This back and forth mechanism 166 includes the roller 162 attached to the holding member 16 and the rack section 164 engaging with the roller 162 attached to the supporting member 12. The back and forth mechanism 166 for forward and backward movement is constructed such that the roller 162 is at the center in the widthwise direction of the holding member 16 and is rotatably supported by the shaft 168. The roller 162 has the gear section (first teeth) 170 formed coaxially with the shaft 168, whose gear 172 engage with the teeth (second teeth) 174 of the rack section 164. The roller 162 partly exposes itself outward through the opening made in the upper surface of the holding member 16.

The rack section 164 is fixed to the surface 20a of the supporting member 12, and extends straight in the lengthwise direction (in the directions of the arrows A, B) of the supporting member 12. The rack section 164 has the teeth 174 arranged in the lengthwise direction on its upper surface facing the gear section 170 of the roller 162.

In order to transfer the sheet-shaped cell culture 30 by means of the biological graft transferring instrument 160, the operator turns the roller 162 (which exposes itself outward from the holding member 16) in a prescribed direction, so that the rack section 164 whose teeth engage with the gear section 170 of the roller 162 moves the supporting member 12 back and forth in the lengthwise direction (in the directions of the arrows A, B). In other words, the rack section 164 converts the rotary action of the roller 162 into the linear action of the supporting member 12 in its lengthwise direction.

Thus, by simple operation of turning the roller 162 of the back and forth mechanism 166, the biological graft transferring instrument 160 can move the forward end 12b of the supporting member 12 back and forth and can transfer the sheet-shaped cell culture 30 from the belt-shaped member 14.

The biological graft transferring instrument and the method for transferring a biological graft are not restricted to those mentioned in the foregoing embodiments but they may be variously changed and modified. The detailed description above describes features and aspects of the biological graft transferring instrument and the method disclosed here. But the invention is not limited to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A biological graft transferring instrument for transferring a biological graft, comprising:
  a main body;
  a displacement member movably positioned relative to the main body, the displacement member having a forward end at one longitudinal end of the displacement member and a base end at an opposite longitudinal end of the displacement member, the displacement member also possessing a front surface and a back surface facing in opposite directions;
  a belt-shaped member possessing first and second ends at opposite longitudinally spaced ends of the belt-shaped member, the first end of the belt-shaped member being secured to the main body so that the first end is fixed in place relative to the main body, the second end of the belt-shaped member being secured to the main body so that the second end is fixed in place relative to the main body, the first and second ends being fixed in position relative to each other;
  the belt-shaped member extending around the front surface and the back surface of the displacement member over a longitudinal extent of the displacement member and extending around the forward end and the base end of the displacement member so that a first portion of the belt-shaped member extending from the first end of the belt-shaped member toward the forward end of the displacement member faces the front surface of the displacement member, so that a second portion of the belt-shaped member extending from the second end of the belt-shaped member toward the base end of the displacement member faces the front surface of the displacement member, and so that a portion of the belt-shaped member between the first and second portions faces the back surface of the displacement member; and
  the first portion of the belt-shaped member being configured to receive the biological graft being placed on the belt-shaped member;
  wherein the main body includes a through hole, and the displacement member passes completely through the through hole so that the displacement member extends outwardly beyond opposite open ends of the through hole;
  wherein the through hole extends along a longitudinal axis of the main body; and
  wherein the main body includes an opening on each longitudinal end thereof and the through hole extends between the openings of both longitudinal ends of the main body.

2. The biological graft transferring instrument according to claim 1, wherein the displacement member includes an operation section fixed to the base end of the displacement member to move together with the displacement member, the operation section being usable by a user to move the displacement member relative to the main body.

3. The biological graft transferring instrument as defined in claim 2, wherein the operation section possesses a three-dimensional rectangular parallelepiped shape and is connected to the base end of the displacement member such that the base end of the displacement member is positioned inside the operation section.

4. The biological graft transferring instrument as defined in claim 1, wherein the belt-shaped member has an outwardly facing holding surface made of a hydrophilic material to hold the biological graft on the holding surface.

5. The biological graft transferring instrument as defined in claim 1, wherein the belt-shaped member has an outwardly facing holding surface
and projections projecting from the holding surface configured to stick into the biological graft.

6. The biological graft transferring instrument as defined in claim 1, wherein the displacement member is hollow shape.

7. The biological graft transferring instrument as defined in claim 1, wherein the displacement member includes a first belt passing opening adjacent to but spaced from the forward end of the displacement member, a portion of the belt-shaped member passing through the first belt passing opening.

8. A biological graft transferring instrument for transferring a biological graft, comprising:
a main body;
a displacement member displaceable relative to the main body, the displacement member possessing a forward end and a base end at opposite ends of the displacement member and a top surface and a bottom surface on opposite sides of the displacement member;
a belt-shaped member wound around the forward end and the base end of the displacement member and fixed to the main body so that the belt-shaped member extends around the top surface, the forward end, the bottom surface, and the base end of the displacement member; and
the biological graft being placed on the belt-shaped member at the forward end of the displacement member;
wherein the main body includes a through hole, and the displacement member passes completely through the through hole so that the displacement member extends outwardly beyond opposite open ends of the through hole;
wherein the through hole extends along a longitudinal axis of the main body; and
wherein the main body includes an opening on each longitudinal end thereof and the through hole extends between the openings of both longitudinal ends of the main body.

9. The biological graft transferring instrument according to claim 8, wherein the displacement member includes an upstanding operation section which is upstanding relative to the displacement member and is fixed to the base end of the displacement member to move together with the displacement member, the operation section being usable by a user to move the displacement member relative to the main body.

10. The biological graft transferring instrument as defined in claim 9, wherein the displacement member includes an operation section possessing a three-dimensional rectangular parallelepiped shape, the operation section being connected to the base end of the displacement member such that the base end of the displacement member is positioned inside the operation section.

11. The biological graft transferring instrument as defined in claim 8, wherein the belt-shaped member has an outwardly facing holding surface made of a hydrophilic material to hold the biological graft on the holding surface.

12. The biological graft transferring instrument as defined in claim 8, wherein the belt-shaped member has an outwardly facing holding surface and projections projecting from the holding surface configured to stick into the biological graft.

13. The biological graft transferring instrument as defined in claim 8, wherein the displacement member is a hollow-shaped displacement member.

14. The biological graft transferring instrument as defined in claim 8, wherein the displacement member includes a first belt passing opening adjacent to but spaced from the forward end of the displacement member, a portion of the belt-shaped member passing through the first belt passing opening.

15. The biological graft transferring instrument as defined in claim 8, wherein the belt-shaped member contacts the forward end and the base end of the displacement member.

\* \* \* \* \*